United States Patent
Ruoslahti et al.

(10) Patent No.: US 7,544,767 B2
(45) Date of Patent: Jun. 9, 2009

(54) HMGN2 PEPTIDES AND RELATED MOLECULES THAT SELECTIVELY HOME TO TUMOR BLOOD VESSELS AND TUMOR CELLS

(75) Inventors: Erkki Ruoslahti, Rancho Santa Fe, CA (US); Kimmo Porkka, Helsinki (FI); Sven Christian, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 717 days.

(21) Appl. No.: 10/400,083

(22) Filed: Mar. 20, 2003

(65) Prior Publication Data

US 2004/0186056 A1 Sep. 23, 2004

Related U.S. Application Data

(60) Provisional application No. 60/453,706, filed on Apr. 5, 2002.

(51) Int. Cl.
*A61K 38/00* (2006.01)
*C07K 16/00* (2006.01)

(52) U.S. Cl. ...................... 530/300; 530/324
(58) Field of Classification Search ................ None
See application file for complete search history.

(56) References Cited

U.S. PATENT DOCUMENTS

| | | | |
|---|---|---|---|
| 5,536,814 A | 7/1996 | Ruoslahti et al. | 530/329 |
| 5,622,699 A | 4/1997 | Ruoslahti et al. | 424/93.6 |
| 6,468,758 B1 | 10/2002 | Benson et al. | |
| 2003/0194754 A1 | 10/2003 | Miller et al. | |

FOREIGN PATENT DOCUMENTS

| EP | 0 135 277 | 3/1985 |
|---|---|---|
| EP | 0 410 537 | 1/1991 |
| EP | 0 639 584 | 2/1995 |
| WO | WO 92/00091 | 1/1992 |
| WO | WO 92/03461 | 3/1992 |
| WO | WO 92/06191 | 4/1992 |
| WO | WO 94/11003 | 5/1994 |
| WO | WO 95/14714 | 6/1995 |
| WO | WO 97/10507 | 3/1997 |
| WO | WO 97/19954 | 6/1997 |
| WO | WO/01/75067 | * 10/2001 |

OTHER PUBLICATIONS

Mathews and Van Holde, Biochemistry, 1996, pp. 165-171.*
Burgess et al, Journal of Cell biology, vol. 111, p. 2129-2138, 1990.*
Lin et al Biochemistry USA, vol. 14, p. 1559-1563, 1975.*
Asai et al., FEBS, vol. 510, p. 206-210, Apr. 2002.*
Porkka et al., PNAS, vol. 99, p. 7444-7449, May 2002.*
Li et al., (Proc. Natl. Acad. Sci: USA 77:3211-3214, 1980.*
Essler et al., PNAS, vol. 99., p. 2252-2257, Feb. 19, 2002.*
Xu et al., "Inhibition of DNA replication and induction of S Phase cell cycle arrest by G-rich oligonucleotides," *J. Biol. Chem.* 276:43221-43230 (2001).
Alfonso et al., "The footprint of chromosomal proteins HMG-14 and HMG-17 on chromatin subunits," *J. Mol. Biol.* 236:189-198 (1994).
Arap et al., "Cancer treatment by targeted drug delivery to tumor vasculature in a mouse model," *Science* 279:377-380 (1998).
Arap et al., "Targeting the prostate for destruction through a vascular address," *Proc. Natl. Acad. Sci. USA* 99:1527-1531 (2002).
Asahara et al., "Isolation of putative progenitor endothelial cells for angiogenesis," *Science* 275:864-967 (1997).
Asahara et al., "VEGF contributes to postnatal neovascularization by mobilizing bone marrow-derived endothelial progenitor cells," *EMBO J.* 18:3964-3972 (1999).
Baillie et al., "Tumor vasculature—a potential therapeutic target," *British J. Cancer* 72:257-267 (1995).
Bergers et al., "Matrix metalloproteinase-9 triggers the angiogenic switch during carcinogenesis," *Nature Cell Biol.* 2:737-744 (2000).
Bicknell, "Vascular targeting and the inhibition of angiogenesis," *Annals of Oncology* 5(Supp. 4): S45-S50 (1994).
Borer et al, "Major nucleolar proteins shuttle between nucleus and cytoplasm," *Cell* 56:379-390 (1989).
Brooks et al., "Integrin $\alpha_v\beta_3$ antagonists promote tumor regression by inducing apoptosis of angiogenic blood vessels," *Cell* 79:1157-1164 (1994).
Burioni et al, "Recombinant human Fab to glycoprotein D neutralizes infectivity and prevents cell-to-cell transmission of herpes simplex viruses 1 and 2 in vitro," *Proc. Natl. Acad. Sci. USA* 91:355-359 (1994).
Burrows and Thorpe, "Vascular targeting—a new approach to the therapy of solid tumors," *Pharmac. Ther.* 64:155-174 (1994).
Bustin, "Regulation of DNA-dependent activities by the functional motifs of the high-mobility-group chromosomal proteins," *Mol. Cell Biol.* 19:5237-5246 (1999).
Bustin and Reeves, "High-mobility-group chromosomal proteins: Architectural components that facilitate chromatin function," *Prog. Nucl. Acid. Res. Mol. Biol.* 54:35-100 (1996).
Carson-Walter et al., "Cell surface tumor endothelial markers are conserved in mice and humans," *Cancer Res.* 61:6649-6655 (2001).
Cattani et al., "Cloning and characterization of human recombinant antibody Fab fragments specific for types 1 and 2 *Herpes simplex* virus," *Microbiologica* 18:135-142 (1995).
Curnis et al., "Enhancement of tumor necrosis factor α antitumor immunotherapeutic properties by targeted delivery to aminopeptidase N (CD13)," *Nature Biotechnology* 18:1185-1190 (2000).

(Continued)

Primary Examiner—Larry R. Helms
Assistant Examiner—Lei Yao
(74) Attorney, Agent, or Firm—McDermott Will & Emery LLP

(57) ABSTRACT

The present invention provides a conjugate which contains a therapeutic moiety linked to a homing molecule that selectively homes to tumor blood vessels and tumor cells and that specifically binds the receptor bound by peptide KDEPQRRSARLSAKPAPPKPEPKPKKAPAKK (SEQ ID NO: 9). Methods of directing a conjugate of the invention to tumor blood vessels and tumor cells and of using a conjugate to treat cancer also are provided.

15 Claims, 12 Drawing Sheets
(6 of 12 Drawing Sheet(s) Filed in Color)

OTHER PUBLICATIONS

Davidoff et al., "Bone marrow-derived cells contribute to tumor neovasculature and, when modified to express an angiogenesis inhibitor, can restrict tumor growth in mice," *Clin. Cancer Res.* 7:2780-2879 (2001).

Deng et al., "Internalization of anti-nucleolin antibody into viable Hep-2 cells," *Mol. Biol. Rep.* 23:191-195 (1996).

Ding et al., "Alleviation of histone H1-mediated transcriptional repression and chromatin compaction by the acidic activation region in chromosomal protein HMG-14," *Mol. Cell Biol.* 17:5843-5855 (1997).

Dvorak et al., "Structure of solid tumors and their vasculature: Implications for therapy with monoclonal antibodies," *Cancer Cells* 3:77-85 (1991).

Fages et al., "Regulation of cell migration by amphoterin," *J. Cell Science* 113:611-620 (2000).

Fawell et al., "Tat-mediated delivery of heterologous proteins into cells," *Proc. Natl.Acad. Sci. USA* 91:664-668 (1994).

Folkman, "Addressing tumor blood vessels," *Nat. Biotech.* 15:510 (1997).

Friedlander et al., "Definition of two angiogenic pathways by distinct $\alpha_v$ integrins," *Science* 270:1500-1502 (1995).

Furka et al., "General method for rapid synthesis of multicomponent peptide mixtures," *Intl. J. Peptide Protein Res.* 37:487-493 (1991).

Gallouzi and Steitz, "Delineation of mRNA export pathways by the use of cell-permeable peptides," *Science* 294:1895-1901 (2001).

Geier et al., "Fate of bacteriophage lambda in non-immune germ-free mice," *Nature* 246:221-223 (1973).

GenBank Accession No. CAB46820 Non-histone chromosomal protein HMG-17 (*Canis familiaris*).

GenBank Accession No. NSBOH7 Non-histone chromosomal protein HMG-17—bovine.

GenBank Accession No. S11349 Non-histone chromosomal protein HMG-17—rat.

Gingrich et al., "Metastatic prostate cancer in a transgenic mouse," *Cancer Res.* 56:4096-4102 (1996).

Ginisty et al., "Structure and functions of nucleolin," *J. Cell Sci.* 112:761-772 (1999).

Goetz et al., "Lu-ECAM-1-mediated adhesion of melanoma cells to endothelium under conditions of flow," *Int. J. Cancer* 65:192-199 (1996).

Goodson et al., "High-affinity urokinase receptor antagonists identified with bacteriophage peptide display," *Proc. Natl. Acad. Sci. USA* 91:7129-7133 (1994).

Hammes et al., "Subcutaneous injection of a cyclic peptide antagonist of vitronectin receptor-type integrins inhibits retinal neovascularization," *Nature Medicine* 2:529-533 (1996).

Hanahan, "Signaling vascular morphogenesis and maintenance," *Science* 277:48-50 (1997).

Hanahan and Folkman, "Patterns and emerging mechanisms of the angiogenic swithc during tumorigenesis," *Cell* 86:353-364 (1996).

Hanahan and Weinberg, "The hallmarks of cancer," *Cell* 100:57-70 (2000).

Hart et al., "Cell Binding and internalization by filamentous phage displaying a cyclic Arg-Gly-Asp-containing peptide," *J. Biol Chem.* 269(17):12468-12474 (1994).

Healy et al., "Peptide ligands for integrin $\alpha_v\beta_3$ selected from random phage display libraries," *Biochem.* 34:3948-3955 (1995).

Holash et al., "Vessel cooption, regression, and growth in tumors mediated by angiopoietins and VEGF," *Science* 284:1994-1998 (1999).

Hori et al., "The receptor for advanced glycation end products (RAGE) is a cellular binding site for amphoterin," *J. Biol. Chem.* 270:25752-25761.

Hornik and Hadas, "Self-encoded, highly condensed solid phase-supported peptide library for identification of ligand-specific peptides," *Chem. Abstracts* 121: Abstract 77731p, React. Polym. 22(3):213-220 (1994).

Hovanessian et al., "The cell-surface-expressed nucleolin is associated with the actin cytoskeleton," *Experimental Cell Research* 261:312-328.

Huang et al., "Tumor infarction in mice by antibody-directed targeting of tissue factor to tumor vasculature," *Science* 275:547-550 (1997).

Hurley, "DNA and its associated processes as targets for cancer therapy," *Nature Reviews Cancer* 2:188-200 (2002).

Jain, "Delivery of molecular and cellular medicine to solid tumors," *Adv. Drug Deliv. Rev.* 26:71-90 (1997).

Kerbel, "Inhibtion of tumor angiogenesis as a strategy to circumvent acquired resistance to anti-cancer therapeutic agents," *BioEssays* 13:31-36 (1991).

Kim et al., "Regulation of angiogenesis in vivo by ligation of integrin $\alpha_5\beta_1$ with the central cell-binding domain of fibronectin," *Am. J. Pathol.* 156:1345-1362 (2000).

Koivunen et al., "Selection of peptides binding to the $\alpha_5\beta_1$ integrin from phage display library," *J. Biol. Chem.* 268:20205-20210 (1993).

Korpelainen and Alitalo, "Signaling angiogenesis and lymphagiogenesis," *Curr. Opin. Cell Biol.* 10:159-164 (1998).

Lappi, "Tumor targeting through fibroblast growth factor receptors," *Sem. Cancer Biology* 6:279-288 (1995).

Lindgren et al., "Cell-penetrating peptides," *Trends. Pharm. Sci.* 21:99-103 (2000).

Martiny-Baron and Marmé, "VEGF-mediated tumor angiogenesis: A new target for cancer therapy," *Current Opin. Biotech.* 6:675-680 (1995).

Miner et al., "Clonal drift of cell surface, melanogenic, and experimental metastatic properties of in vivo-selected, brain meninges-colonizing murine B16 melanoma," *Cancer Res.* 42:4631-4638 (1982).

Mitjans et al., "An anti-$\alpha v$-integrin antibody that blocks integrin function inhibits the development of a human melanoma in nude mice," *J. Cell Sci.* 108:2825-2838 (1995).

Mueller et al., "Pre-clinical therapy of human melanoma with morpholino-doxorubicin conjugated to a monoclonal antibody directed agains an integrin on melanoma cells," *Chemical Abstracts* 115(21):222872 (1991).

Nagy et al., "Cytotoxic analogs of luteinizing hormone-releasing hormone containing doxorubicin or 2-pyrrolinodoxorubicin, a derivative 500-1000 times more potent," *Proc. Natl. Acad. Sci. USA* 93:7269-7273 (1996).

Nilsson et al., "Targeted delivery of tissue factor to the ED-B domain of fibronectin, a marker of angiogensis, mediates the infarction of solid tumors in mice," *Cancer Res.* 61:711-716 (2001).

Ozerdem et al., "NG2 proteoglycan is expressed exclusively by mural cells during vascular morphogenesis," *Dev. Dyn.* 222:218-227 (2001).

Pasqualini and Ruoslahti, "Organ targeting in vivo using phage display peptide libraries," *Nature* 380:364-366 (1996).

Pasqualini et al., "Aminopeptidase N is a receptor for tumor-homing peptides and a target for inhibiting angiogensis," *Cancer Res.* 60:722-727 (2000).

Pasqualini et al., "$\alpha v$ Integrins as receptors for tumor targeting by circulating ligands," *Nature Biotechnology* 15:542-546 (1997).

Pauli et al., "Organ-preference of metastasis," *Cancer and Metastasis Reviews* 9:175-189 (1990).

Porkka et al., "A fragnebt if the HMGN2 protein homes to the nuclei of tumor cells and tumor endothelial cells in vivo," *Proc. Natl. Acad. Sci. USA* 99:7444-7449 (2002).

Rajotte et al., "Molecular heterogeneity of the vascular endothelium revealed by in vivo phage display," *J. Clin. Invest.* 102:430-437 (1998).

Rak et al., "Consequences of angiogenesis for tumor progression, metastasis and cancer therapy," *Anti-Cancer Drugs* 6:3-18 (1995).

Roghani and Moscatelli, "Basic fibroblast growth factor is internalized through both receptor-mediated and heparan sulfate-mediated mechanisms," *J. Biol. Chem.* 267:22156-22162 (1992).

Ruoslahti and Rajotte, "An address system in the vasulature of normal tissues and tumors," *Ann. Rev. Immunol.* 18:813-827 (2000).

Ruoslahti, "RGD and other recognition sequences for integrins," *Annu. Rev. Cell Dev. Biol.* 12:697-715 (1996).

Ruoslahti, "Targeting tumor vasculature with homing peptides from phage display," *Sem. Cancer Biol.* 10:435-442 (2000).

Said et al., "The anti-HIV cytokine midkine binds the cell surface-expressed nucleolion as a low affinity receptor," *J. Biol. Chem.* 277:37492-37502 (2002).

Schlingemann et al., "Expression of the high molecular weight melanoma-associated antigen by pericytes during angiogenesis in tumors and in healing wounds," *Am. J. Pathol.* 136:1393-1405 (1990).

Schmidt-Zachmann and Nigg, "Protein localization to the nucleolus: a search for targeting domains in nucleolin," *J. Cell Sci.* 105:799-806 (1993).

Schwarze et al., "In vivo protein transduction: Delivery of a biologically active protein into the mouse," *Science* 285:1569-1572 (1999).

Shibata et al., "Nuclear targeting by the growth factor midkine," *Mol. Cell Biol.* 22:6788-6796 (2002).

Silletti et al., "Disruption of matrix metalloproteinase 2 binding to integrin $\alpha_v\beta_3$ by an organic molecule inhibits angiogenesis and tumor growth in vivo," *Proc. Natl. Acad. Sci. USA* 98:119-124 (2001).

Sinclaid and O'Brien, "Cell surface-localized nucleolin is a eukaryotic receptor for the adhesin intimin-gamma of enterohemorrhagic *Escherichia coli* 0157:H7," *J. Biol. Chem.* 277:2876-2885 (2002).

Srivastava and Pollard, "Molecular dissection of nucleolin's role in growth and cell proliferation: new insights," *FASEB J.* 13:1911-1922 (1999).

St Croix et al., "Genes expressed in human tumor endothelium," *Science* 289:1197-1202 (2000).

Suzuki et al., "Possible existence of common internalization mechanisms among arginine-rich peptides," *J. Biol. Chem.* 277:2437-2443 (2002).

Taguchi et al., "Blockade of RAGE-amphoterin signalling suppresses tumour growth and metastases," *Nature* 405:354-360 (2000).

Trieschmann et al., "Modular structure of chromosomal proteins HMG-14 and HMG-17: Definition of a transcriptional enhancement domain distinct from the nucleosomal binding domain," *Mol. Cell Biol.* 15:6663-6669 (1995).

Tsutsui et al, "A new family of heparin-binding growth/differentiation factors: increased midkine expression in Wilms' tumor and other human carcinomas," *Cancer Res.* 53:1281-1285 (1993).

Yancopoulos et al., "Vascular-specific growth factors and blood vessel formation," *Nature* 407:242-248 (2000).

Walker et al., "The partial amino acid sequence of a non-histone chromosomal protein," *Biochem Biophys Res Commun*, 73:72-78 (1976).

\* cited by examiner

US 7,544,767 B2

HMGN2 PEPTIDES AND RELATED MOLECULES THAT SELECTIVELY HOME TO TUMOR BLOOD VESSELS AND TUMOR CELLS

This application claims benefit of the filing date of U.S. Provisional Application No. 60/453,706, filed Apr. 5, 2002, which was converted from U.S. Ser. No. 10/116,866, and which is incorporated herein by reference.

This invention was made with government support under CA 74238, CA 82713 and CA 30199 awarded by the National Cancer Institute and DAMD 17-02-1-0315 and DAMD 17-98-1-8164, both awarded by the Department of Defense. The government has certain rights in this invention.

BACKGROUND OF THE INVENTION

1. Field of the Invention

The present invention relates generally to the fields of cancer, molecular medicine and drug delivery and, more specifically, to molecules that selectively home to tumor blood vessels and tumor cells.

2. Background Information

A major hurdle to advances in treating cancer is the lack of agents that are effective in selectively targeting a cancer while sparing normal tissue. Radiation therapy and surgery, for example, which generally are localized treatments, can cause substantial damage to normal tissue in the treatment field, resulting in scarring and loss of normal tissue. Chemotherapy, in comparison, which generally is administered systemically, can cause substantial damage to organs such as bone marrow, mucosa, skin and the small intestine, which undergo rapid cell turnover and continuous cell division. As a result, undesirable side effects such as nausea, loss of hair and drop in blood cell count occur as a result of systemic treatment with a chemotherapeutic agent. Such undesirable side effects often limit the amount of drug that can be safely administered, thereby hampering survival rate and impacting the quality of patient life.

Anticancer agents that target DNA are some of the most effective agents in clinical use and are responsible for significant increases in the survival of cancer patients when administered in combination with other drugs. Effective anticancer agents that target DNA include alkylating agents and agents that intercalate into DNA or result in double-stranded DNA breaks. Exemplary DNA-targeted drugs in use or clinical trial today are cyclophosphamide, melphalan, mitomycin C, bizelesin, cisplatin, doxorubicin, etoposide, mitoxantrone, actinomycin D and bleomycin (Hurley, *Nature Reviews Cancer* 2:188-200 (2002)). Unfortunately, like many other anti-cancer agents, DNA-targeted drugs are extremely toxic and result in significant side effects (Slapak and Kufe in *Harrison's Principles of Internal Medicine* 14$^{th}$ Edition pages 523-537 McGraw-Hill, Inc. New York 1998). As an example, use of the platinum agent, cisplatin, can be limited by severe nausea, vomiting, neuropathy and myelosuppression.

Selective delivery of DNA-targeting drugs and other anticancer agents to tumor cells or the vasculature that supports tumor growth would result in less toxic therapy since rapidly proliferating normal cells would be spared. However, to date, it has been difficult to produce drugs that target cancer-specific genes or that are delivered specifically to cancer cells or supporting vasculature. Thus, there is a need for molecules that selectively target tumor cells and tumor vasculature. The present invention satisfies this need and also provides related advantages.

SUMMARY OF THE INVENTION

The present invention provides an isolated homing molecule that selectively homes to tumor blood vessels and tumor cells and that specifically binds nucleolin, where the molecule is not a peptide having a length of more than 85 residues. A homing molecule of the invention can be, for example, a peptide or peptidomimetic.

The present invention also provides an isolated peptide or peptidomimetic having a length of less than 85 residues that contains the amino acid sequence KDEPQRRSARLSAKPA-PPKPEPKPKKAPAKK (SEQ ID NO: 9) or a peptidomimetic of this sequence. In one embodiment, the invention provides an isolated peptide having a length of less than 85 residues that contains the amino acid sequence KDEPQRRSARLSAKPAPPKPEPKPKKAPAKK (SEQ ID NO: 9). An isolated peptide or peptidomimetic of the invention can have, for example, a length of less than 50 residues or a length of less than 35 residues.

Further provided herein is an isolated homing peptide or peptidomimetic of less than 85 residues that selectively homes to tumor blood vessels and tumor cells and that specifically binds nucleolin. In one embodiment, such an isolated homing peptide or peptidomimetic includes the amino acid sequence KDEPQRRSARLSAKPAPPKPEPKPKKAPAKK (SEQ ID NO: 9) or a conservative variant or peptidomimetic of this sequence. In another embodiment, the isolated homing peptide or peptidomimetic of the invention that specifically binds nucleolin is a peptide. In further embodiments, such an isolated homing peptide or peptidomimetic has a length of less than 50 residues or a length of less than 35 residues.

The present invention further provides a conjugate which contains a therapeutic moiety linked to a homing molecule that selectively homes to tumor blood vessels and tumor cells and that specifically binds nucleolin. In one embodiment, such a conjugate contains a homing molecule which is not an antibody or antigen-binding fragment thereof such as an anti-nucleolin antibody or antigen-binding fragment. In another embodiment, the conjugate contains a peptide or peptidomimetic portion having a length of at most 200 residues. In a further embodiment, the conjugate contains a peptide or peptidomimetic portion having a length of at most 50 residues.

A homing molecule incorporated into a conjugate of the invention can be, for example, a homing peptide or peptidomimetic. In one embodiment, a conjugate of the invention includes a homing peptide or peptidomimetic containing the amino acid sequence SEQ ID NO: 9 or a conservative variant or peptidomimetic of this sequence. Such a homing peptide or peptidomimetic can include, for example, the amino acid sequence SEQ ID NO: 9, or a peptidomimetic thereof. In another embodiment, a conjugate of the invention includes a homing peptide or peptidomimetic which contains the amino acid sequence SEQ ID NO: 11 or a conservative variant or peptidomimetic thereof. Such a homing peptide or peptidomimetic can include, for example, the amino acid sequence SEQ ID NO: 11, or a peptidomimetic of this sequence.

A variety of therapeutic moieties are useful in the conjugates of the invention, including, without limitation, anti-angiogenic agents and cytotoxic agents, such as those that target a DNA-associated process. A cytotoxic agent that targets a DNA-associated process can be, for example, an alkylating agent, an anti-tumor antibiotic or a sequence-selective agent. As non-limiting examples, cytotoxic agents that target a DNA-associated process encompass cyclophosphamide, melphalan, mitomycin C, bizelesin, cisplatin, doxorubicin, etoposide, mitoxantrone, SN-38, Et-743, actinomycin D, bleomycin and TLK286.

If desired, a conjugate of the invention can be multivalent, including at least two homing molecules that each selectively homes to tumor blood vessels and tumor cells and that each specifically blind nucleolin. In particular embodiments, a conjugate of the invention includes at least ten or at least 100 of such homing molecules. A variety of therapeutic moieties are useful in the multivalent conjugates of the invention including, but not limited to, phage moieties.

In a further embodiment, the invention provides a multivalent conjugate containing at least two homing peptides or peptidomimetics that each selectively homes to tumor blood vessels and tumor cells and that each independently contains the amino acid sequence SEQ ID NO: 9 or a conservative variant or peptidomimetic of this sequence. In one embodiment, such a conjugate contains at least ten homing peptides or peptidomimetics that each selectively homes to tumor blood vessels and tumor cells and that each independently contains the amino acid sequence SEQ ID NO: 9 or a conservative variant or peptidomimetic thereof. In another embodiment, a conjugate of the invention contains at least 100 homing peptides or peptidomimetics that each selectively homes to tumor blood vessels and tumor cells and that each independently contains the amino acid sequence SEQ ID NO: 9 or a conservative variant or peptidomimetic thereof. Any of the above multivalent conjugates of the invention can include a variety of therapeutic moieties, for example, a phage moiety.

Also provided herein is a conjugate containing a detectable label linked to a homing molecule that selectively homes to tumor blood vessels and tumor cells and that specifically binds nucleolin. A variety of detectable labels are useful in such a conjugate including radionuclides and fluorescent labels.

The present invention also provides a method of directing a therapeutic moiety to tumor blood vessels and tumor cells in a subject by administering to the subject a conjugate which contains a therapeutic moiety linked to a homing molecule that selectively homes to tumor blood vessels and tumor cells and that specifically binds nucleolin, thereby directing the therapeutic moiety to tumor blood vessels and tumor cells. In one embodiment, the homing molecule is not an antibody or antigen-binding fragment thereof. In other embodiments, the peptide or peptidomimetic portion of the conjugate has a length of at most 200 residues, or a length of at most 50 residues.

A variety of homing molecules are useful in the methods of the invention including homing peptides and peptidomimetics. A method of directing a therapeutic moiety to tumor blood vessels and tumor cells in a subject can be practiced, for example, using a homing peptide or peptidomimetic that contains the amino acid sequence SEQ ID NO: 9, or a conservative variant or peptidomimetic of this sequence. In one embodiment, such a homing peptide or peptidomimetic includes the amino acid sequence SEQ ID NO: 9, or a peptidomimetic thereof. A method of directing a therapeutic moiety to tumor blood vessels and tumor cells in a subject also can be practiced, for example, with a homing peptide or peptidomimetic which contains the amino acid sequence SEQ ID NO: 11, or a conservative variant or peptidomimetic of this sequence. In one embodiment, the method is practiced with a conjugate containing a homing peptide or peptidomimetic that includes the amino acid sequence SEQ ID NO: 11 or a peptidomimetic thereof.

A variety of therapeutic moieties can be directed to tumor blood vessels and tumor cells in a subject according to a method of the invention. Such moieties encompass, without limitation, anti-angiogenic agents and cytotoxic agents, including cytotoxic agents that target a DNA-associated process such as alkylating agents, anti-tumor antibiotics and sequence-selective cytotoxic agents. In particular embodiments, a method of the invention relies on one of the following cytotoxic agents that target a DNA-associated process: cyclophosphamide, melphalan, mitomycin C, bizelesin, cisplatin, doxorubicin, etoposide, mitoxantrone, SN-38, Et-743, actinomycin D, bleomycin or TLK286.

The present invention also provides a method of imaging tumors and tumor vasculature in a subject by administering to the subject a conjugate containing a detectable label linked to a homing molecule that selectively homes to tumor blood vessels and tumor cells and that specifically binds nucleolin; and detecting the conjugate, thereby imaging tumors and tumor vasculature. A homing molecule useful in an imaging method of the invention can be, for example, a homing peptide or peptidomimetic such as a homing peptide or peptidomimetic that contains the amino acid sequence SEQ ID NO: 9 or a conservative variant or peptidomimetic of this sequence. Any of a variety of detectable labels are useful in the imaging methods of the invention, including fluorescent labels and radionuclides such as indium-111, technetium-99, carbon-11, and carbon-13.

The present invention also provides a method of reducing the number of tumor blood vessels in a subject by administering to the subject a conjugate which contains a cytotoxic agent linked to a homing molecule that selectively homes to tumor blood vessels and tumor cells and that specifically binds nucleolin, thereby reducing the number of tumor blood vessels in the subject. The peptide or peptidomimetic portion of the conjugate can have, for example, a length of at most 200 residues, or a length of at most 50 residues. In one embodiment, a method of the invention is practiced with a conjugate containing a homing peptide or peptidomimetic. In a further embodiment, a method of the invention is practiced with a conjugate containing a homing peptide or peptidomimetic that includes the amino acid sequence SEQ ID NO: 9, or a conservative variant or peptidomimetic of this sequence. Any of the therapeutic moieties described above, such as anti-angiogenic agents, cytotoxic agents and cytotoxic agents that target a DNA-associated process, as well as additional moieties disclosed herein or known in the art, can be used to reduce the number of tumor blood vessels according to a method of the invention.

Also provided herein is a method of treating cancer in a subject by administering to the subject a conjugate which contains a therapeutic moiety linked to a homing molecule that selectively homes to tumor blood vessels and tumor cells and that specifically binds nucleolin. In particular embodiments, the peptide or peptidomimetic portion of the conjugate has a length of at most 200 residues, or a length of at most 50 residues. In other embodiments, a method of the invention is practiced with a conjugate containing a homing peptide or peptidomimetic such as a homing peptide or peptidomimetic that includes the amino acid sequence SEQ ID NO: 9, or a conservative variant or peptidomimetic of this sequence. It is understood that, in a method of the invention for treating cancer in a subject, any of a variety of therapeutic moieties can be useful, including but not limited to, anti-angiogenic agents; cytotoxic agents; and cytotoxic agents that target a DNA-associated process.

The present invention further provides a method of isolating progenitor cells from a heterogeneous mixture of cells by contacting the heterogenous mixture of cells with a homing molecule that selectively homes to tumor blood vessels and tumor cells and specifically binds nucleolin under conditions suitable for specific binding of the homing molecule to the progenitor cells; and separating cells that bind the homing molecule from non-binding cells, thereby isolating progenitor cells from the heterogenous mixture of cells. The heterogeneous mixture of cells can be, for example, primary tissue such as primary bone marrow.

In one embodiment, isolation of progenitor cells according to a method of the invention is practiced with a homing peptide or peptidomimetic. In a further embodiment, the method is practiced with a homing peptide or peptidomimetic containing the amino acid sequence KDEPQRRSARLSAK-PAPPKPEPKPKKAPAKK (SEQ ID NO: 9) or a conservative variant or peptidomimetic thereof. In another embodiment, the method is practiced with a homing peptide or peptidomimetic containing the amino acid sequence SEQ ID NO: 11 or a conservative variant or peptidomimetic thereof. Homing peptides and peptidomimetics useful in isolating progenitor cells can have a variety of lengths, including, without limitation, a length of less than 85 residues, a length of less than 50 residues, or a length of less than 35 residues.

A method of the invention for isolating progenitor cells can be practiced, if desired, with a homing molecule attached to a support. A method of the invention also can be practiced, for example, with a homing molecule linked to a fluorescent label. In one embodiment, the separation step includes fluorescence activated cell sorting (FACS). In further embodiments, progenitor cells are isolated using a homing peptide or peptidomimetic containing the amino acid sequence SEQ ID NO: 9 or SEQ ID NO: 11, or a conservative variant or peptidomimetic of one of these sequences, linked to a fluorescent label.

The present invention also provides a method of isolating one or more homing molecules that selectively home to tumor blood vessels and tumor cells by contacting nucleolin, or a fragment thereof, with a library of molecules under conditions suitable for specific binding of a molecule to nucleolin; assaying for specific binding; and separating one or more nucleolin-binding molecules from the library, thereby isolating one or more homing molecules that selectively home to tumor blood vessels and tumor cells. In one embodiment, a screening method of the invention is practiced by assaying for specific binding to purified nucleolin. In another embodiment, a screening method of the invention is practiced by assaying for specific binding to a fragment of nucleolin including the NCL3 domain. In yet another embodiment, a screening method of the invention is practiced by assaying for specific binding to cells expressing nucleolin on the cell surface and further assaying for specific binding to control cells which do not express cell-surface nucleolin.

BRIEF DESCRIPTION OF THE DRAWINGS

This patent or application file contains at least one color photograph. Copies of this patent or patent application publication with the color photographs will be provided by the Patent & Trademark Office upon request and payment of the necessary fee.

DETAILED DESCRIPTION OF THE INVENTION

The present invention is directed to the discovery of homing molecules which selectively home to tumor blood vessels and tumor cells, for example, to leukemia and breast cancer cells and their vasculature, in preference to most non-tumor tissue. A homing molecule of the invention also can selectively home, as described further below, to cells that act as progenitors of tumor vasculature.

As disclosed herein, a screening strategy was developed to identify molecules that recognize an epitope shared by endothelial progenitor cells within the bone marrow and by tumor endothelial cells. By pre-selection for binding to lineage-depleted bone marrow cells (putative progenitor cells) ex vivo and further selection for homing to HL-60 xenograft tumors in vivo, a selected phage pool was produced showing 20-fold enrichment for tumor homing in vivo relative to the unselected cDNA library (see Example I and FIG. 1). The predominant cDNA in the selected phage pool (SEQ ID NO: 5) was a fragment encoding the first 73 residues of the high mobility group protein HMGN2, a highly conserved nucleosomal protein involved in unfolding higher-order chromatin structure and facilitating transcriptional activation of mammalian genes. In addition to the predominant cDNA, additional HMGN2 clones isolated from the selected phage pool (SEQ ID NOS: 1 to 4) all shared a common sequence corresponding to exons 3 and 4 of HMGN2 (see FIG. 2A).

Figures 2A, 2B:
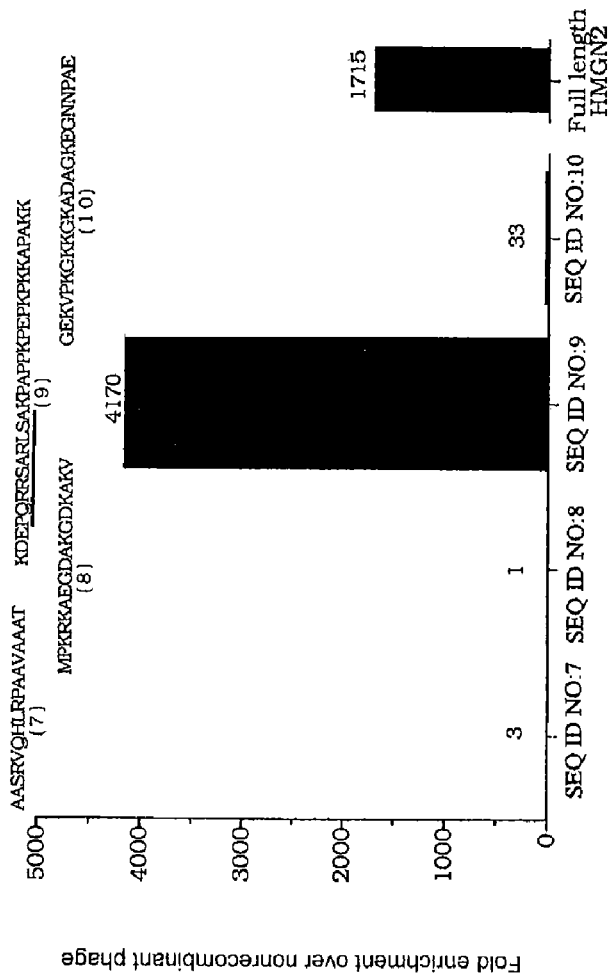
FIG. 2 shows characterization of HMGN2 clones and localization of the HMGN2 cell binding domain. (A) Amino acid sequences of five isolated human HMGN2 clones (SEQ ID NOS: 1 to 5) with SEQ ID NOS indicated in parenthesis to the left. The corresponding portion of human HMGN2 from Genbank accession M12623 (Swissprot accession P05204) is shown as SEQ ID NO: 6. Intron-exon boundaries of the gene are marked with arrows, and the sequence encoded by exon 3 of HMGN2 is underlined. (B) The sequence and cell binding activity of four fragments (SEQ ID NOS: 7 to 10) corresponding to portions of SEQ ID NO: 5. SEQ ID NOS are indicated in parentheses above or below the sequence. Phage binding to primary tumor cells obtained from HL-60 xenograft tumors was assayed; the results are represented as fold enrichment relative to non-recombinant T7 phage. The number of plaque forming units (pfu) are indicated above each column. One experiment representative of four is shown.

As further disclosed herein, phage displaying a set of sequences corresponding to fragments of the amino-terminal portion of HMGN2 were constructed to localize the HMGN2 domain responsible for cell binding and in vivo homing. This set of phage was tested for activity in binding to primary cells from HL-60 xenograft tumors. As shown in FIG. 2B, when phage bearing fragment SEQ ID NO: 7, 8, 9 or 10 were tested for tumor binding activity as compared to non-recombinant phage, only phage bearing the 31-amino acid fragment encoded by exons 3 and 4 (SEQ ID NO: 9), which corresponds to the nucleosomal binding domain of HMGN2, demonstrated substantial tumor cell binding activity (see Example II). Furthermore, binding of SEQ ID NO: 9-displaying phage to tumor cells was inhibited by free SEQ ID NO: 9 peptide in a dose dependent fashion, indicating that the phage binding was specific. Furthermore, phage expressing a subsequence of SEQ ID NO: 9 (PQRRSARLSA; SEQ ID NO: 11) exhibited a 90-fold binding preference for tumor cells as compared to non-recombinant phage.

As further disclosed herein in Example III, fluorescein-conjugated SEQ ID NO: 9 was injected into the tail vein of mice bearing HL-60 or MDA-MB-435 xenografts. Histological analysis showed a strong fluorescent signal in tumor tissue, whereas little or no specific fluorescence was detected in normal brain, liver or spleen. Within the HL-60 leukemia tumor tissue, SEQ ID NO: 9 localized to tumor cells and cells lining tumor blood vessels, indicating that SEQ ID NO: 9 binding is a shared property of tumor cells and tumor endothelial cells. Furthermore, peptide SEQ ID NO: 9 selectively homed to a variety of tumor types; selective homing was observed with all tumor types tested, including HL-60 leukemia, MDA-MB-435 breast cancer and TRAMP mouse prostate carcinoma. In sum, the results disclosed herein with fluorescein and rhodamine conjugates of SEQ ID NO: 9, as well as phage-displayed SEQ ID NO: 9, indicate that this HMGN2-derived peptide can be used to target a moiety such as a drug to tumors and tumor vasculature.

Figure 3:
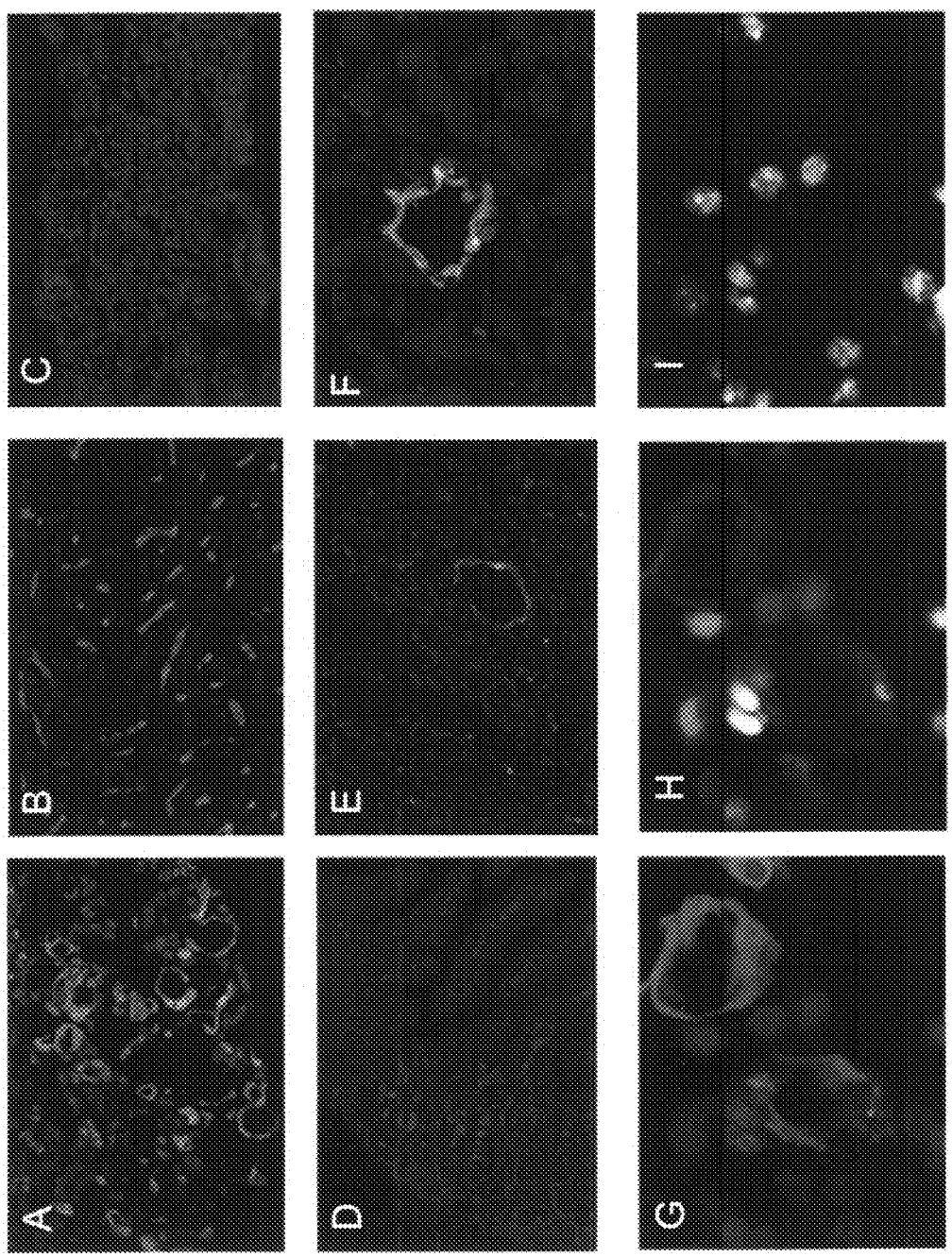
FIG. 3 shows tissue localization of intravenously injected HMGN2 peptide SEQ ID NO: 9. All panels except panel (E) show immunofluorescence of tissue samples from mice injected with fluorescein-labeled peptide SEQ ID NO: 9. (A) HL-60 tumor; (B) brain; (C) skin; (D) gut; (E) fluorescein-labeled ARALPSQRSR (SEQ ID NO: 13) control peptide in mice bearing HL-60 xenograft; (F) MDA-MB-435 tumor; (G) a higher magnification view from panel A showing the localization of SEQ ID NO: 9 (green), lectin stained vasculature (red) and DAPI stained nuclei (blue). Green and blue images are shown individually in panels H and I. Magnification: panels A, B and E, 200×; panels C and D, 100×; and panels F-I, 400×.
Figure 5:
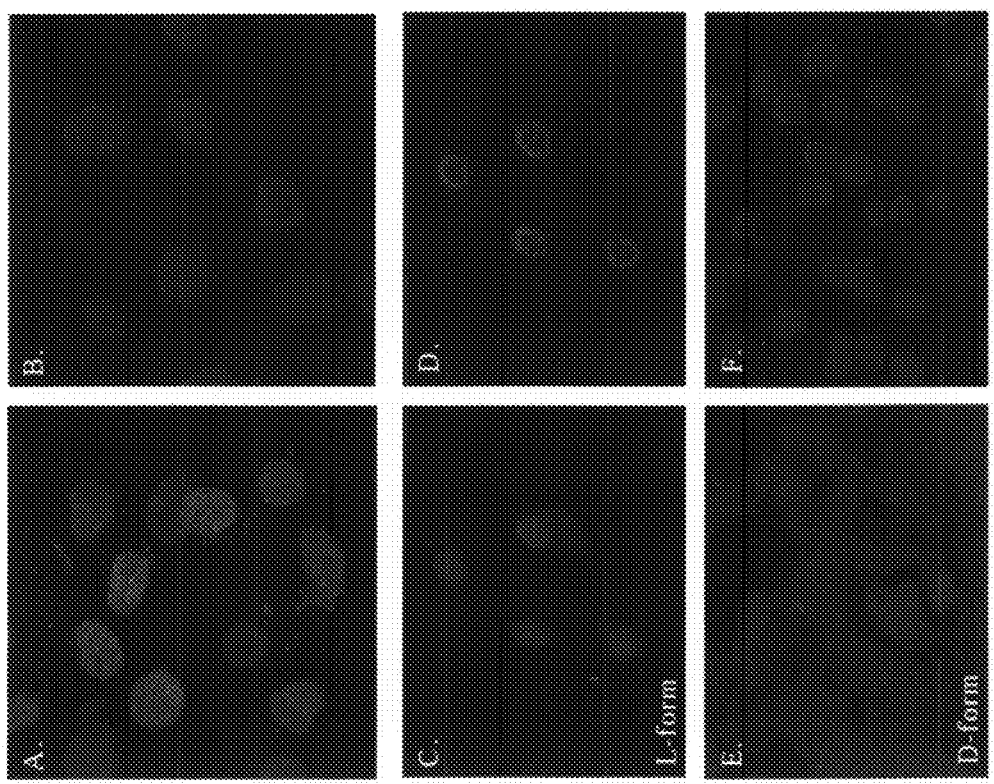
FIG. 5 shows uptake and nuclear translocation of peptide SEQ ID NO: 9 in cultured tumor cells. HL-60 cells were incubated with (A) fluorescein-labeled SEQ ID NO: 9 or (B) fluorescein-labeled ARALPSQRSR (SEQ ID NO: 13) control peptide, stained with DAPI (blue) and examined by confocal microscopy. (C-F) MDA-MB-435 cells incubated with peptide SEQ ID NO: 9 synthesized either from (C and D) L amino acids or (E and F) D amino acids, stained with DAPI and examined under an epifluorescent microscope. Panels (C) and (E) were analyzed using a green (FITC) filter; panels (D) and (F) were analyzed using a blue (DAPI) filter. Magnification (A) and (B), 400×; C-F, 200×.

As further disclosed herein, fluorescein-labeled SEQ ID NO: 9 accumulated in the nucleus of target cells in vivo and in vitro (see FIGS. 3 and 5). For example, cultured HL-60 or MDA-MB-435 cells incubated with 1 μM fluorescein-labeled SEQ ID NO: 9 revealed nuclear peptide localization within 30 minutes. These results demonstrate that peptide SEQ ID NO: 9 localizes to the nuclei of tumor and endothelial cells upon internalization.

Figure 6:
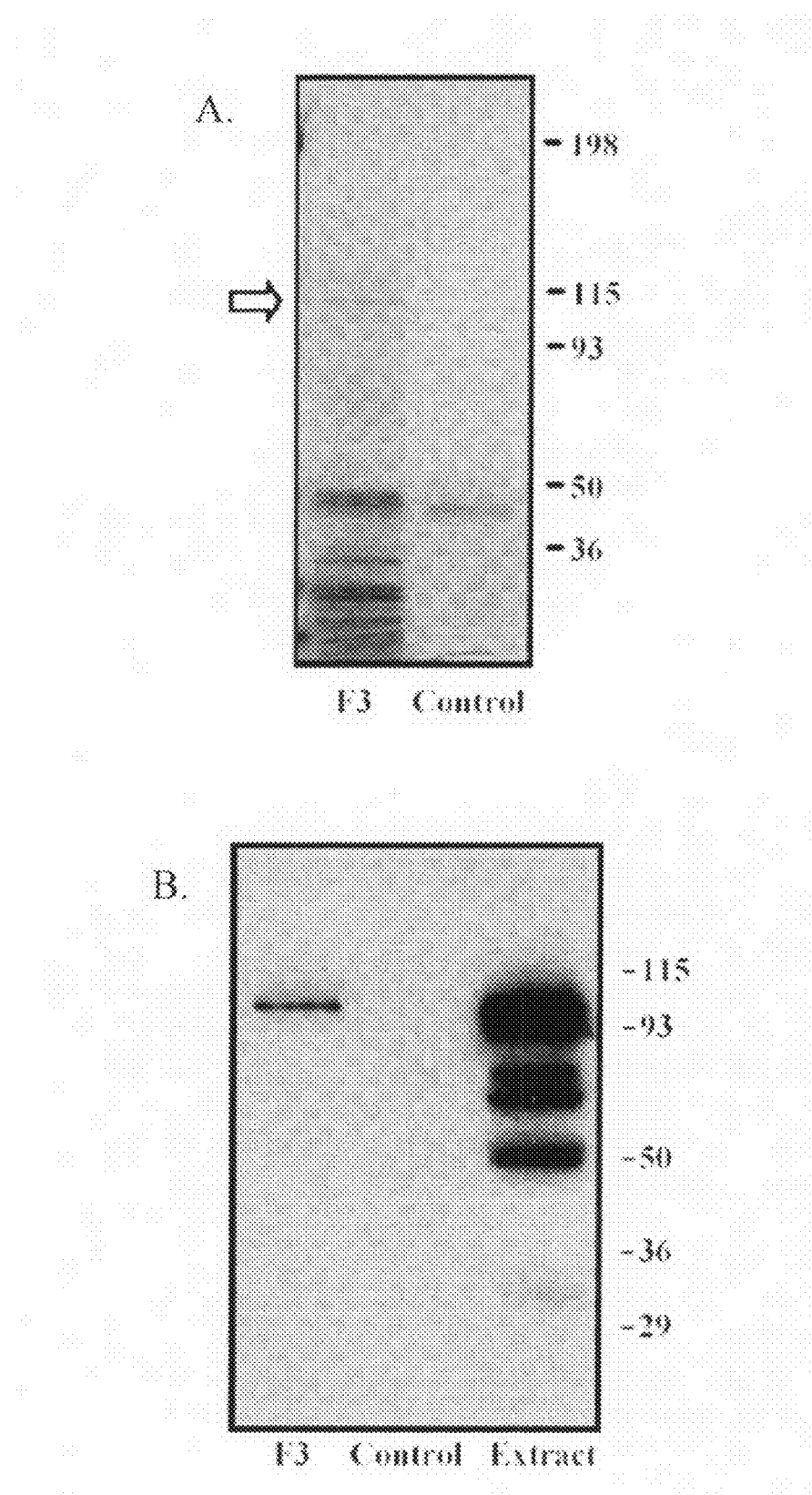
FIG. 6 shows that nucleolin binds to immobilized peptide SEQ ID NO: 9. (A) SDS gel electrophoresis of proteins isolated from MDA-MB-435 cell extracts on SEQ ID NO: 9 affinity matrix ("F3") or control matrix ("control"). The arrow indicates a specific 110-kDa band, which was identified as nucleolin by mass spectroscopy. (B) Immunoblotting of eluates from peptide SEQ ID NO: 9 ("F3") and control peptide affinity matrices and unfractionated MDA-MB-435 cell extract ("extract") with a murine monoclonal anti-nucleolin antibody.

Additional results disclosed herein demonstrate that the cell surface molecule recognized by HMGN2-derived peptides such as SEQ ID NO: 9 is cell-surface nucleolin and that internalization of peptide SEQ ID NO: 9 is entirely dependent on cell surface expression of nucleolin. As disclosed in Example VI, affinity chromatography of MDA-MB-435 cell extracts revealed a major band of about 110 kDa, which was identified by spectrometric analysis as nucleolin (FIG. 6A).

Figure 10:
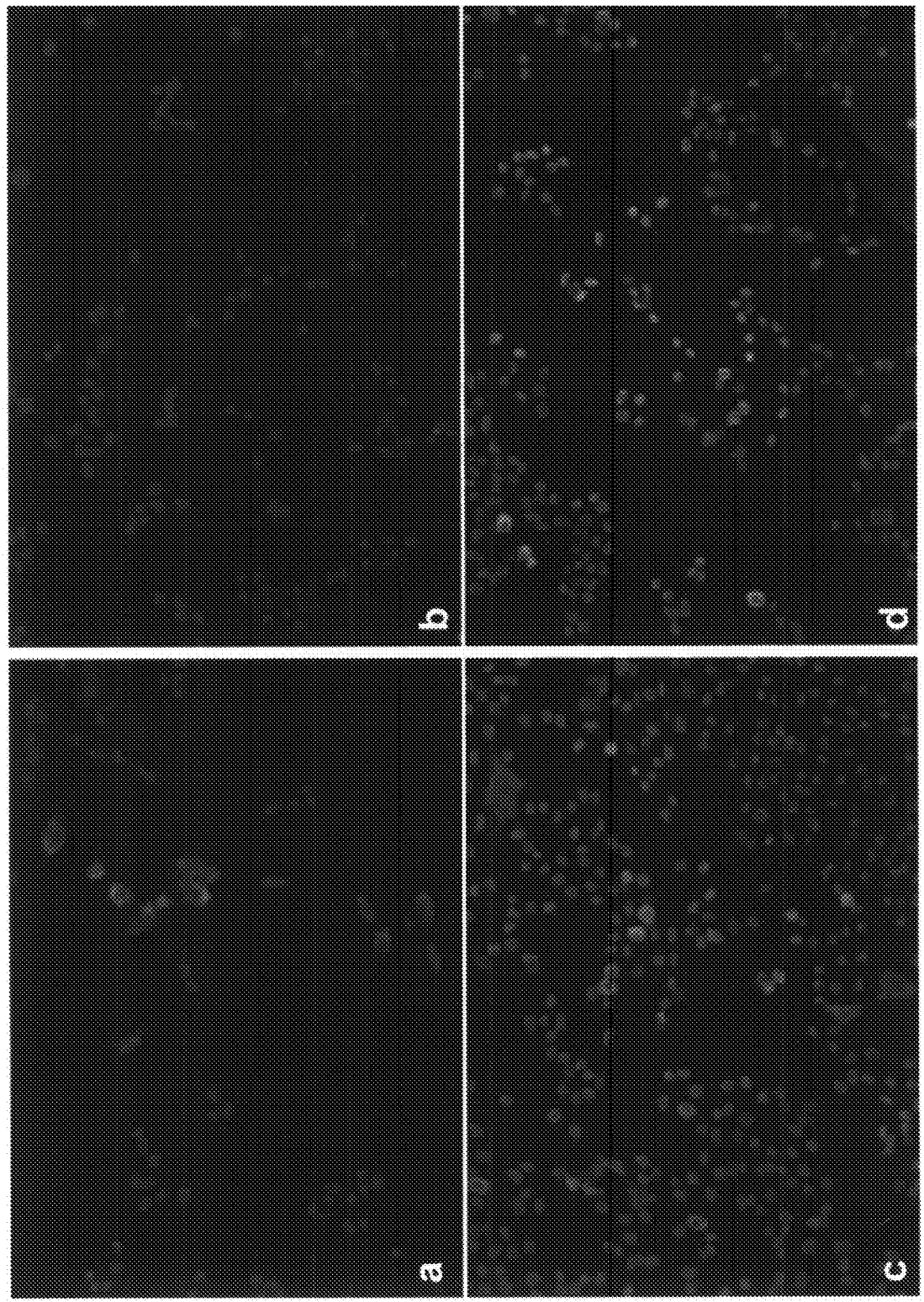
FIG. 10 shows the subcellular distribution of nucleolin in dividing and stationary cells. MDA-MB-435 cells were stained with NCL3 anti-nucleolin polyclonal antibody (red) and counter-stained with 4',6-diamidino-2-phenylindole (DAPI; blue) after growth in media with or without fetal calf serum and in both intact and permeabilized cells. (A) Fixed, intact cells cultured in standard media (B) Fixed, intact cells which were serum starved. (C) Triton X-100-permeabilized cells cultured in standard media. (D) Triton X-100-permeabilized cells which were serum starved.
Figure 11:
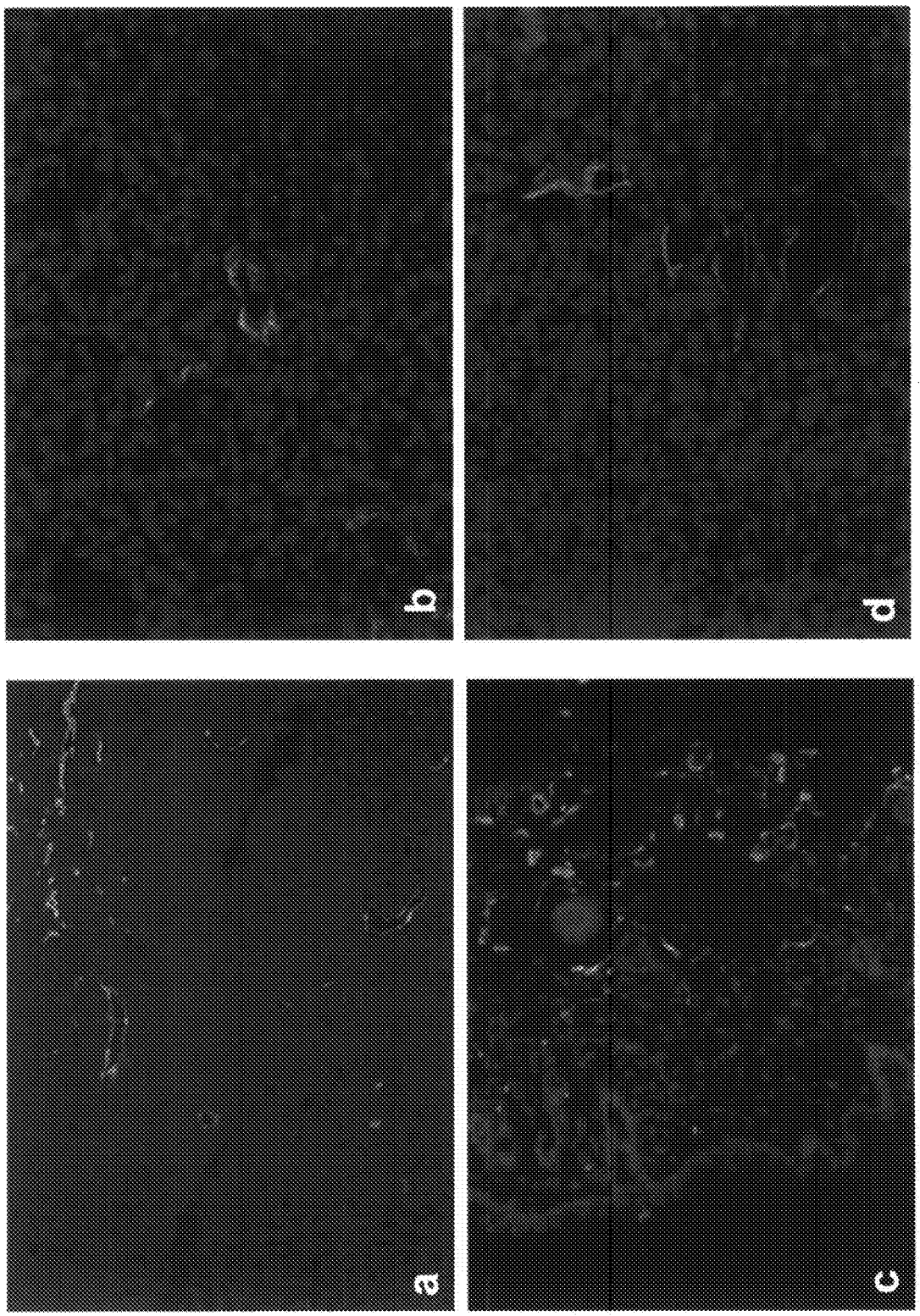
FIG. 11 shows that cell surface nucleolin is specific for tumor blood vessels in vivo. Mice bearing MDA-MB-435 xenograft tumors were intravenously injected with polyclonal anti-nucleolin antibodies. Tumor and control organs were removed one hour following injection, and sectioned and examined for nucleolin staining. Blood vessels were stained with anti-CD31 antibody (green), and nuclei were counterstained with DAPI (blue). (A,B) Tumor blood vessels from mice injected with anti-nucleolin. (C) Blood vessels of the skin from mice injected with anti-nucleolin. (D) Tumor blood vessels from mouse injected with control rabbit IgG. Magnification: A, C and D, ×200; B, ×400.

Furthermore, anti-nucleolin antibodies and cell-surface biotin labeling indicated that nucleolin is expressed on the surface of actively growing cells, but is exclusively nuclear in serum-starved non-dividing cells (see FIG. 10). Thus, cell surface expression of nucleolin is associated with active cell proliferation. Both uptake of peptide SEQ ID NO: 9 and staining of intact cells with anti-nucleolin antibodies were suppressed in serum-starved cells. In addition, HL-60 leukemia cells induced to differentiate in culture in non-proliferating macrophage lose the ability to internalize peptide SEQ ID NO: 9. As further disclosed herein, nucleolin was expressed at the cell surface in tumor vasculature in vivo (FIG. 11). These results indicate that exprssion of cell surface nucleolin and the ability to bind and internalize HMGN2-derived peptides such as SEQ ID NO: 9 is much more restricted in vivo than in vitro. These results demonstrate that HMGN2-derived peptides such as peptide SEQ ID NO: 9 and other molecules that bind nucleolin can be useful for selectively targeting anti-angiogenic agents or other anti-cancer therapeutics into the nucleus of tumor cells as well as tumor endothelial cells.

Thus, the present invention relates, in part, to the surprising discovery that a peptide derived from HMGN2, which is one of the high mobility group (HMG) proteins, can selectively accumulate in tumors and tumor vasculature upon intravenous administration. HMGN2 (HMG-17) is a relatively abundant protein expressed in the nuclei of all higher eukaryotes, that functions in unfolding of higher-order chromatin structure and in facilitating transcriptional activation in mammals (Bustin, *Mol. Cell. Biol.* 19:5237-5246 (1999)). As a group, the HMG proteins are abundant, ubiquitous proteins that bind to DNA in a sequence-independent manner. The HMG proteins can be divided into three subfamilies, the HMG-1/2 subfamily; the HMG-I/Y subfamily and the HMG-14/17 subfamily, each of which have a characteristic functional sequence motif which is the main site of interaction between the HMG protein and the DNA or chromatin target (Bustin, supra, 1999).

HMGN2 belongs to the HMG-14/17 subfamily, which contains HMG proteins characterized by a nucleosomal binding domain that specifically recognizes the generic structure of the 146 bp nucleosome core (Bustin and Reeves, *Prog. Nucl. Acids Res. Mol. Biol.* 54:35-100 (1996)). HMGN2 binds to nucleosomes cooperatively via the nucleosomal binding domain to form a homodimeric complex, and the carboxy terminal region of HMGN2 mediates changes in chromatin structure (Ding et al., *Mol. Cell. Biol.* 17:5843-5855 (1997); Trieschmann et al., *Mol. Cell. Biol.* 15:6663-6669 (1995)). The major sites of interaction between HMGN2 and the nucleosomal core DNA are located 25 bp from the end of the DNA and in the two major grooves flanking the nucleosomal dyad axis (Alfonso et al., *J. Mol. Biol.* 236:189-198 (1994)). The nucleosomal binding domain motif is a positively charged stretch of approximately 30 amino acids with a bipartite structure: the highly conserved amino-terminal region of the nucleosomal binding domain is enriched in arginine residues, while the carboxy-terminal region contains a preponderance of lysine and proline (Bustin and Reeves, supra, 1996).

HMGN2 functions to enhance transcription and replication, although only from chromatin and not from DNA templates, indicating that this protein acts as a modifier of chromatin structure rather than as a polymerase-specific factor. Enhancement of DNA-dependent activities is associated with decompaction of the nucleosome array in the chromatin fiber; both transcriptional regulation and chromatin decompaction are mediated by the negatively charged C-terminal domain of HMGN2 (Ding et al., supra, 1996; Trieschmann et al., supra, 1995). This C-terminal domain contacts the amino-terminal tail of histone H3, near the lysine residues serving as targets for histone acetyltransferases, and also targets histone H1.

Based on the above findings, the present invention provides an isolated peptide or peptidomimetic having a length of less than 85 residues that contains the amino acid sequence KDEPQRRSARLSAKPAPPKPEPKPKKAPAKK (SEQ ID NO: 9) or a peptidomimetic of this sequence. In one embodiment, the invention provides an isolated peptide having a length of less than 85 residues that contains the amino acid sequence SEQ ID NO: 9. An isolated peptide or peptidomimetic of the invention can have, for example, a length of less than 50 residues or a length of less than 35 residues.

The invention also provides an isolated homing peptide or peptidomimetic of less than 85 residues that selectively homes to tumor blood vessels and tumor cells and contains the amino acid sequence SEQ ID NO: 9 or a conservative variant or peptidomimetic of this sequence. In one embodiment such an isolated homing peptide or peptidomimetic is a peptide. In other embodiments, the peptide or peptidomimetic has a length of less than 50 residues or a length of less than 35 residues.

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

The peptides and peptidomimetics of the invention, including the bifunctional, multivalent and homing peptides and peptidomimetics discussed below, can have a variety of lengths. A peptide or peptidomimetic of the invention can have, for example, a relatively short length of less than eight, nine, ten, 12, 15, 20, 25, 30, 35, 40, 45, 50, 60, 70 or 80 residues. A peptide or peptidomimetic of the invention also can be useful in the context of a significantly longer sequence as described further below. As used herein, the term "residue" refers to amino acids or analogs thereof. It is understood that a peptide containing, for example, the amino acid sequence SEQ ID NO: 9 includes the specified amino acids as a contiguous sequence not separated by other amino acids.

The present invention also provides an isolated peptide or peptidomimetic containing an amino acid sequence which is a conservative variant, for example, of the sequence KDEPQRRSARLSAKPAPPKPEPKPKKAPAKK (SEQ ID NO: 9). As used herein, a "conservative variant" is an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

As disclosed herein, a peptide or peptidomimetic of the invention can maintain homing activity in the context of a significantly longer sequence. For example, the 31-mer peptide KDEPQRRSARLSAKPAPPKPEPKPKKAPAKK (SEQ ID NO: 9) maintained the ability to home when fused to a phage coat protein, confirming that a peptide of the invention can have selective homing activity when embedded in a larger protein sequence. Thus, the invention further provides a chimeric protein containing a peptide or peptidomimetic of the invention, or a homing peptide or peptidomimetic of the invention, fused to a heterologous protein. In one embodiment, the invention provides a chimeric protein containing a homing peptide or peptidomimetic that selectively homes to tumor blood cells or tumor cells and that specifically binds nucleolin fused to a heterologous protein. In one embodiment, the heterologous protein has a therapeutic activity. In a further embodiment, the heterologous protein is an antibody or antigen-binding fragment thereof. In other embodiments, the invention provides a chimeric protein in which a peptide or peptidomimetic containing the amino acid sequence SEQ ID NO: 9, or a conservative variant or peptidomimetic of this sequence, is fused to a heterologous protein. The term "heterologous," as used herein in reference to a protein fused to a peptide or peptidomimetic of the invention, means a protein derived from a source other than the gene encoding the peptide of the invention or upon which the peptidomimetic is derived. A chimeric protein of the invention can have a variety of lengths, for example, up to 100, 200, 300, 400, 500, 800, 1000 or 2000 residues or more.

The invention also provides a bifunctional peptide which contains a homing peptide that selectively homes to tumor blood cells or tumor cells and that specifically binds nucleolin, fused to a second peptide having a separate function. Such bifunctional peptides have at least two functions conferred by different portions of the peptide and can, for example, display anti-angiogenic activity or pro-apoptotic activity in addition to selective homing activity. As a non-limiting example, the invention provides a bifunctional peptide having the sequence KDEPQRRSARLSAKPAPPKPEPKPKKA-PAKK-GG-$_D$(KLAKLAK)$_2$ (SEQ ID NO: 21).In such a peptide, the KDEPQRRSARLSAKPAPPKPEPKPKKAPAKK (SEQ ID NO: 9) portion exhibits selective homing activity, while the $_D$(KLAKLAK)$_2$ (SEQ ID NO: 14)portion exhibits pro-apoptotic activity.

The present invention further provides an isolated multivalent peptide or peptidomimetic that includes at least two motifs each independently containing the amino acid sequence SEQ ID NO: 9, or a conservative variant or peptidomimetic thereof. The multivalent peptide or peptidomimetic can have, for example, at least three, at least five or at least ten of such motifs, each independently containing the amino acid sequence SEQ ID NO: 9, or a conservative variant or peptidomimetic thereof. In particular embodiments, the multivalent peptide or peptidomimetic has two, three, four, five, six, seven, eight, nine, ten, fifteen or twenty identical or non-identical motifs of the amino acid sequence SEQ ID NO: 9, or a conservative variant or peptidomimetic thereof. In another embodiment, the multivalent peptide or peptidomimetic contains identical motifs, which consist of the amino acid sequence SEQ ID NO: 9, or a conservative variant or peptidomimetic of this sequence. In a further embodiment, the multivalent peptide or peptidomimetic contains contiguous motifs, which can be identical or non-identical.

Thus, the invention provides peptides and peptidomimetics, including bifunctional and multivalent peptides and peptidomimetics, and homing peptides and peptidomimetics as discussed further below. As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids, and have an activity such as selective homing activity of the peptide upon which the peptidomimetic is derived (see, for example, Goodman and Ro, *Peptidomimetics for Druq Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an $N^\alpha$-$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an N-$C^\delta$ or $C^\alpha$-$C^\delta$ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crystallogr.* Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide of the invention, for example, with activity in selectively homing to tumor blood vessels and tumor cells.

An isolated peptide or peptidomimetic of the invention, or a homing peptide, peptidomimetic or molecule of the invention as discussed further below, can be cyclic, or otherwise conformationally constrained. As used herein, a "conformationally constrained" molecule, such as a peptide or peptidomimetic, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization.

As used herein in reference to a peptide or peptidomimetic, the term cyclic refers to a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. Methods of cyclization include formation of a disulfide bond between the side-chains of non-adjacent amino acids or amino acid analogs; formation of a lactam bond, for example, between a side-chain group of one amino acid or analog thereof to the N-terminal amine of the amino-terminal residue; and formation of lysinonorleucine and dityrosine bonds.

Active fragments of the homing peptide disclosed herein as SEQ ID NO: 9 also can be useful in the conjugates and methods of the invention. As used herein in reference to a peptide sequence such as SEQ ID NO: 9, the term "active fragment" means a fragment that has substantially the amino acid sequence of a portion of the 31-amino acid peptide SEQ ID NO: 9 and that retains substantially the selective homing activity of the parent peptide. Selective homing activity can be assayed by routine methods, as described in the Examples below. In one embodiment, an active fragment contains the amino acid sequence of a portion of SEQ ID NO: 9. Such an active fragment can have, for example, the amino acid sequence of at least 10, 12, 15, 18, 20, 22, 25, or 28 contiguous residues of SEQ ID NO: 9.

As disclosed herein, peptide SEQ ID NO: 9 recognizes a target "receptor" which is expressed on tumor cells as well as blood vessel cells of tumors but which is not significantly expressed or available for binding in most normal tissues. The cell surface and cell-type selective expression of the target receptor, which is disclosed herein as nucleolin, form the basis for the selective homing activity of peptide SEQ ID NO: 9 and related peptides, peptidomimetics and other molecules. Based on this discovery, it is clear that molecules structurally unrelated to SEQ ID NO: 9 but which also bind cell surface nucleolin also have the same characteristic of selectively homing to tumor blood vessels and tumor cells. Such molecules can be identified by the ability to specifically bind to, or compete for binding to, purified nucleolin, or to compete with SEQ ID NO: 9 for binding to nucleolin-expressing cells such as MDA-MB-435 cells, as described further below. Selective homing to tumor blood vessels and tumor cells readily can be confirmed using in vivo panning as disclosed herein in Example I (see, also, U.S. Pat. No. 5,622,699).

Thus, the present invention provides a method of reducing the number of tumor blood vessels in a subject by administering to the subject an anti-nucleolin antibody or antigen-binding fragment thereof, which is internalized by tumor endothelial cells. Anti-nucleolin antibodies useful in the invention include, without limitation, monoclonal antibodies, humanized antibodies and antibodies against an acidic portion of the amino-terminal domain of nucleolin, which general classes are not mutually exclusive.

The invention further provides a method of treating cancer in a subject by administering to the subject an anti-nucleolin antibody or antigen-binding fragment thereof, which is internalized by tumor cells. Anti-nucleolin antibodies useful for treating cancer according to a method of the invention include, without limitation, monoclonal antibodies, humanized antibodies and antibodies against an acidic portion of the amino-terminal domain of nucleolin.

Nucleolin, an abundant nucleolar protein that plays an important role in ribosome biogenesis, was initially known as C23 (Orrick et al., *Proc. Natl. Acad. Sci., USA* 70:1316-1320 (1973)). This ubiquitous protein is encoded by a gene on chromosome 12 with the characteristic GC-rich promoter sequences found in housekeeping genes. Nucleolin regulates ribosome biogenesis and maturation, has a demonstrated helicase activity, and also has been implicated in chromatin decondensation, cytoplasmic/nuclear transport of ribosomal components and pre-ribosomal particles, cytokinesis, replication, embryogenesis and nucleogenesis. Nucleolin also appears to bind specifically to several nuclear proteins, such as nucleophosmin (B23), topoisomerase 1 and the growth factor midkine (Ginisty et al., *J. Cell Science* 112:761-772 (1999)).

Nucleolin has an apparent molecular weight of 100 to 110 kDa, and nucleolin cDNAs are predicted to encode proteins of about 713 amino acids. In addition to the human sequence, homologs have been identified in hamster, rat, mouse and chicken (LaPeyre et al., *Proc. Natl. Acad. Sci. Usa* 84:1472-1476 (1987); Srivastava et al., *FEBS Letters* 250:99-105 (1989); Bourbon et al., *J. Mol. Biol.* 200:627-638 (1988); and Maridor and Nigg, *Nucleic Acids Res.* 18:1286 (1990)). In nature, nucleolin is highly phosphorylated and methylated and may be ADP-ribosylated. Analysis of the amino acid sequence of nucleolin reveals three structural domains. The amino-terminal domain, which controls rRNA transcription, is made up of highly acidic regions interspersed with basic sequences and contains multiple phosphorylation sites. Acidic α-helical structures within this domain may bind histone H1. The central globular domain, which contains four RNA-binding domains known as RBD or RRM, controls pre-RNA processing. The carboxy-terminal domain, denoted the GAR or RGG domain, is rich in glycine, arginine and phenylalanine residues, contains high levels of $N^G,N^G$-dimethylarginines and functions in nucleolar localization (Ginisty et al., supra, 1999).

As used herein, the term "nucleolin" means a polypeptide having substantially the amino acid sequence of a known nucleolin such as human, murine, rat, hamster or chicken nucleolin. As a non-limiting example, nucleolin can have substantially the amino acid sequence of human nucleolin (SEQ ID NO: 19). As described above, a full-length nucleolin includes an amino-terminal acidic domain and a central globular domain. One skilled in the art appreciates that a fragment of a nucleolin polypeptide, for example, retaining one or more amino-terminal acidic stretches, also can be useful in generating internalizing anti-nucleolin antibodies or in screening for homing molecules that selectively home to tumor cells or tumor vasculature, as described hereinbelow.

The term nucleolin encompasses a polypeptide having the sequence of a naturally occurring human nucleolin (SEQ ID NO: 19), and includes related polypeptides having substantial amino acid sequence similarity to SEQ ID NO: 19. Such related polypeptides typically exhibit greater sequence similarity to nucleolin than to other helicases or nucleolar proteins and include, but are not limited to, species homologies and isotype variants. The term nucleolin generally describes polypeptides having an amino acid sequence having greater than about 40% amino acid sequence identity with human nucleolin (SEQ ID NO: 19). In particular, a nucleolin can have greater than 50% amino acid identity, greater than 60% amino acid identity, greater than 70% amino acid identity, greater than 80% amino acid identity, or greater than 85%, 90% or 95% amino acid identity with the human nucleolin sequence SEQ ID NO: 19.

Anti-nucleolin antibodies can be useful as homing molecules in the conjugates and methods of the invention and further can be useful in unconjugated form as anti-tumor and anti-angiogenic agents. As used herein, the term "antibody" is used in its broadest sense to include polyclonal and monoclonal antibodies, as well as polypeptide fragments of antibodies that retain binding activity for nucleolin of at least about $1 \times 10^5$ M$^{-1}$. One skilled in the art understands that anti-nucleolin antibody fragments including, without limitation, Fab, F(ab')$_2$ and Fv fragments, can retain binding activity for nucleolin and, thus, are included within the definition of antibody. In addition, the term "antibody," as used herein, encompasses non-naturally occurring antibodies and fragments usually containing, at a minimum, one $V_H$ and one $V_L$ domain, such as chimeric antibodies, humanized antibodies and single chain Fv fragments (scFv) that specifically or selectively bind nucleolin. Such non-naturally occurring antibodies can be constructed using solid phase peptide synthesis, produced recombinantly or obtained, for example, by screening phage-displayed or other combinatorial libraries such as those consisting of variable heavy and light chains as described in Borrebaeck (Ed.), *Antibody Engineering* (Second edition) New York: Oxford University Press (1995)) using, for example, an assay described herein below.

Anti-nucleolin antibodies also can be prepared using a nucleolin fusion protein or a synthetic peptide encoding a portion of nucleolin such as the NCL3 domain or another acidic portion of the amino-terminal region of nucleolin as an immunogen (see Example VI). One skilled in the art understands that purified human or other nucleolin, which can be produced recombinantly, for example, using the human nucleolin nucleic acid sequence disclosed herein as SEQ ID NO: 18, or full-length or fragments of nucleolin, including peptide portions of nucleolin such as synthetic peptide fragments of the human nucleolin amino acid sequence disclosed herein as SEQ ID NO: 19, can be used as immunogens. It is understood that fragments of nucleolin useful as immunogens include the NCL3 domain and related and different fragments of nucleolin that serve to produce nucleolin antibodies which are readily internalized into cells expressing cell-surface nucleolin. One skilled in the art further understands that non-immunogenic fragments or synthetic peptides of nucleolin can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988)).

Anti-nucleolin antibodies useful in the invention further encompass commercially available and other anti-nucleolin antibodies known in the art such as, without limitation, the murine anti-human nucleolin monoclonal 4E2 from AMS Biotechnology Ltd. (United Kingdom) or Research Diagnostics Inc. (Flanders, N.J.); the MS3 anti-human monoclonal (U.S. Pat. No. 4,902,615); and the D3 anti-human monoclonal (Deng et al., *Mol. Biol. Rep*. 23:191-195 (1996); and Hovanessian et al., *Exp. Cell Res*. 261:312-328 (2000)).

Thus, it is clear that a homing molecule useful in the invention can be an HMGN2-derived peptide or an unrelated nucleolin-binding molecule such as an anti-nucleolin antibody, midkine or basic fibroblast growth factor (bFGF), or a fragment, peptide or peptidomimetic derived therefrom. As an example, an antibody that binds to the acidic domain at the amino-terminus of nucleolin (NCL3) is internalized by cells, whereas an antibody that binds to another site on nucleolin is not, indicating that an anti-NCL3 or related similar anti-nucleolin antibody can be useful for targeting and internalizing linked therapeutic agents.

Midkine is a 13 kDa cytokine related to pleiotropin which plays a role in neurite outgrowth and neuronal differentiation and is overexpressed in some human carcinomas. Midkine appears to bind nucleolin through the RGG domain or negatively charged amino-terminal domain. Like the nucleolin-binding peptide SEQ ID NO: 9, midkine is highly basic and binds to heparin sulfate. One skilled in the art understands that full-length midkine or bFGF or fragments or peptidomimetics derived from that retain the ability to bind nucleolin also can selectively home to tumor vasculature and tumor cells in the same manner as disclosed herein for the HMGN2-derived peptide, SEQ ID NO: 9. In one embodiment, the invention is practiced with a midkine or bFGF-derived peptide or peptidomimetic with nucleolin-binding activity but without the cytokine activity of native midkine or bFGF.

Also provided herein is a method of isolating one or more homing molecules that selectively home to tumor blood vessels and tumor cells by contacting nucleolin, or a fragment thereof, with a library of molecules under conditions suitable for specific binding of a molecule to nucleolin; assaying for specific binding; and separating one or more nucleolin-binding molecules from the library, thereby isolating one or more homing molecules that selectively home to tumor blood vessels and tumor cells. Cells that express nucleolin on the cell surface as well as purified nucleolin, or a fragment thereof, can be useful in the screening methods of the invention. As non-limiting examples, native, recombinant and human nucleolin, and fragments of human nucleolin such as the amino-terminal acidic domain (NCL3) and other SEQ ID NO: 9-binding fragments of nucleolin, whether purified or expressed on the surface of a cell, can be useful in the screening methods of the invention. Libraries that can be screened according to a method of the invention include, but are not limited to, libraries of peptides and peptidomimetics, libraries of small molecules, and libraries of antibodies and antigen-binding fragments thereof, including synthetic, single-chain or other antibody libraries. In one embodiment, a method of the invention includes a further step of assaying for internalization of one or more molecules of the library into a cell expressing cell surface nucleolin or a fragment thereof. As an example, where the library is a library of antibodies, the method can further include assaying for internalization of one or more nucleolin-binding antibodies into a cell expressing cell-surface nucleolin or a fragment thereof. Where a fragment of nucleolin is utiliized in place of full-lenght nucleolin, it is understood that such a nucleolin fragment is a fragment sufficient for internalization of a nucleolin-binding molecule such as peptide SEQ ID NO: 9 or an anti-NCL3 antibody.

Based on the restricted cell surface expression of nucleolin and tumor vessels and tumor cells in vivo, the present invention provides methods of selectively directing an anti-cancer or anti-angiogenic agent to tumor vessels and tumor cells by administering a nucleolin-binding molecule linked to the anti-cancer or anti-angiogenic agent. The invention also provides a method of treating cancer by administering a cytotoxic agent linked to a nucleolin-binding molecule, thereby destroying tumor endothelial cell precursors. Further provided herein are methods of treating cancer and methods of reducing tumor angiogenesis by reducing cell surface expression of nucleolin.

The present invention also provides an isolated homing molecule that selectively homes to tumor blood vessels and tumor cells and that specifically binds nucleolin, where the molecule is not a peptide having a length of more than 85 residues. A homing molecule of the invention can be, for example, a peptide or peptidomimetic.

The invention also provides an isolated homing peptide or peptidomimetic of less than 85 residues that selectively homes to tumor blood vessels and tumor cells and that specifically binds nucleolin. In one embodiment, such an isolated homing peptide or peptidomimetic includes the amino acid sequence KDEPQRRSARLSAKPAPPKPEPKPKKAPAKK (SEQ ID NO: 9) or a conservative variant or peptidomimetic of this sequence. In another embodiment, the isolated homing peptide or peptidomimetic of the invention that specifically binds nucleolin is a peptide. In further embodiments, such an isolated homing peptide or peptidomimetic has a length of less than 50 residues or a length of less than 35 residues.

As used herein, the term "molecule" is used broadly to mean a polymeric or non-polymeric organic chemical such as a small molecule drug; a nucleic acid molecule such as an RNA, a cDNA or an oligonucleotide; a peptide or peptidomimetic; or a protein such as an antibody or a growth factor receptor or a fragment thereof such as an Fv, Fd, or Fab fragment of an antibody containing the antigen-binding domain.

The term "homing molecule" as used herein, means any molecule that selectively localizes in vivo to the tumor blood vessels and tumor cells of one or more tumors in preference to most non-tumor tissues. Similarly, the term "homing peptide" or "homing peptidomimetic" means a peptide or peptidomimetic that selectively localizes in vivo to the tumor blood vessels and tumor cells of one or more tumors in preference to most non-tumor tissues. It is understood that a homing molecule that selectively homes in vivo to tumor blood vessels and tumor cells can home to all tumor types and their supporting blood vasculature or can exhibit preferential homing to the blood vessels and tumor cells of a subset of tumor types.

By "selectively homes" is meant that, in vivo, the homing molecule, peptide or peptidomimetic binds preferentially to tumor blood vessels and tumor cells, such as leukemias and breast carcinomas and their supporting blood vasculature, as compared to most non-tumor tissue. Selective homing generally is characterized by at least a two-fold greater localization within tumor blood vessels and tumor cells, such as such as leukemias and breast carcinomas and their supporting blood vasculature, as compared to a non-tumor tissue such as brain, spleen and liver tissue. A homing molecule can be characterized by 5-fold, 10-fold, 20-fold or more preferential localization to tumor blood vessels and tumor cells as compared to brain, spleen or liver, or as compared to many or most non-tumor tissues. As disclosed herein, the homing molecule SEQ ID NO: 9 selectively homed to a small population of cells within skin, gut and bone marrow, and it is understood that a homing molecule can home, in part, to one or more non-tumor tissues or to a small population of cells within one or more non-tumor tissues in addition to selectively homing to tumor blood vessels and tumor cells.

A homing molecule of the invention specifically binds nucleolin. As used herein, the term "specifically binds" or "specifically binding" means binding that is measurably different from a non-specific interaction. Specific binding can be measured, for example, by determining binding of a molecule compared to binding of a control molecule, which generally is a molecule of similar structure that does not have binding activity. In this case, specific binding is indicated if the molecule has measurably higher affinity for cells expressing cell-surface nucleolin, for example, HL-60 or MDA-MB-435 cells, than for cells that do not express cell-surface nucleolin. Specificity of binding can be determined, for example, by competitive inhibition of the binding of a known binding molecule such as SEQ ID NO: 9 or SEQ ID NO: 11.

The term "specifically binding," as used herein, includes both low and high affinity specific binding. Specific binding can be exhibited, for example, by a low affinity homing molecule having a Kd of at least about $10^{-4}$ M. For example, if nucleolin has more than one binding site, a homing molecule having low affinity can be useful for targeting tumor blood vessels and tumor cells. Specific binding also can be exhibited by a high affinity homing molecule, for example, a homing molecule having a Kd of at least about $10^{-5}$ M. Such a molecule can have, for example, a Kd of at least about $10^{-6}$ M, at least about $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful and are encompassed by the invention. Low affinity homing molecules are useful in targeting, for example, multivalent conjugates such as viruses and other particles. High affinity homing molecules are useful in targeting, for example, multivalent and univalent conjugates.

The invention further provides a conjugate which contains a therapeutic moiety linked to a homing molecule that selectively homes to tumor blood vessels and tumor cells and that specifically binds nucleolin. In one embodiment, such a conjugate contains a homing molecule which is not an antibody or antigen-binding fragment thereof. In another embodiment, the peptide or peptidomimetic portion of the conjugate has a length of at most 200 residues. In a further embodiment, the peptide or peptidomimetic portion of the conjugate has a length of at most 50 residues.

A homing molecule incorporated into a conjugate of the invention can be, for example, a homing peptide or peptidomimetic. In one embodiment, a conjugate of the invention includes a homing peptide or peptidomimetic containing the amino acid sequence SEQ ID NO: 9 or a conservative variant or peptidomimetic of this sequence. Such a homing peptide or peptidomimetic can include, for example, the amino acid sequence SEQ ID NO: 9, or a peptidomimetic thereof. In another embodiment, a conjugate of the invention includes a homing peptide or peptidomimetic which contains the amino acid sequence SEQ ID NO: 11 or a conservative variant or peptidomimetic thereof. Such a homing peptide or peptidomimetic can include, for example, the amino acid sequence SEQ ID NO: 11, or a peptidomimetic of this sequence.

A variety of therapeutic moieties are useful in the conjugates of the invention, including, without limitation, anti-angiogenic agents and cytotoxic agents, such as those that target a DNA-associated process. A cytotoxic agent that targets a DNA-associated process can be, for example, an alkylating agent, an anti-tumor antibiotic or a sequence-selective agent. As non-limiting examples, cytotoxic agents that target a DNA-associated process encompass cyclophosphamide, melphalan, mitomycin C, bizelesin, cisplatin, doxorubicin, etoposide, mitoxantrone, SN-38, Et-743, actinomycin D, bleomycin and TLK286.

Also provided herein is a conjugate containing a detectable label linked to a homing molecule that selectively homes to tumor blood vessels and tumor cells and that specifically binds nucleolin. A variety of detectable labels are useful in such a conjugate including radionuclides and fluorescent labels.

In one embodiment, a conjugate of the invention includes a homing molecule that is not an antibody or antigen-binding fragment thereof. "Antibody" is an art-recognized term that refers to a peptide or polypeptide containing one or more complementarity determining regions (CDRs). See, for example, Borrabaeck, *Antibody Engineering* 2nd Edition, Oxford University Press, New York (1995).

In another embodiment, the peptide or peptidomimetic portion of the conjugate has a defined length. The peptide or peptidomimetic portion of the conjugate can have, for example, a length of at most 10, 20, 30, 40, 50, 100, 150, 200, 250, 300, 400, 500, 600, 700, 800, 900, 1000 or 2000 residues. It is understood that the term "peptide or peptidomimetic portion of the conjugate" means total number of residues in the homing peptide or peptidomimetic and any contiguous protein, peptide or peptidomimetic, such as a therapeutic protein or pro-apoptotic peptide.

If desired, a conjugate of the invention can be multivalent, including at least two homing molecules that each selectively homes to tumor blood vessels and tumor cells and that specifically binds nucleolin. In particular embodiments, a multivalent conjugate of the invention includes at least ten or at least 100 of such homing molecules. A variety of therapeutic moieties are useful in the multivalent conjugates of the invention including, but not limited to, phage moieties.

In a further embodiment, the invention provides a multivalent conjugate containing at least two homing peptides or peptidomimetics that each selectively homes to tumor blood vessels and tumor cells and that each independently contains the amino acid sequence SEQ ID NO: 9 or a conservative variant or peptidomimetic of this sequence. In one embodiment, such a conjugate contains at least ten homing peptides or peptidomimetics that each selectively homes to tumor blood vessels and tumor cells and that each independently contains the amino acid sequence SEQ ID NO: 9 or a conservative variant or peptidomimetic thereof. In another embodiment, a conjugate of the invention contains at least 100 homing peptides or peptidomimetics that each selectively homes to tumor blood vessels and tumor cells and that each independently contains the amino acid sequence SEQ ID NO: 9 or a conservative variant or peptidomimetic thereof. Any of the above multivalent conjugates of the invention can include a variety of therapeutic moieties, for example, a phage moiety.

A multivalent conjugate of the invention containing multiple homing molecules can include, for example, two or more, three or more, five or more, ten or more, twenty or more, thirty or more, forty or more, fifty or more, 100 or more, 200 or more, 300 or more, 400 or more, 500 or more or 100 or more homing molecules. In one embodiment, the homing molecules have an identical amino acid sequence. In another embodiment, the multivalent conjugate includes homing molecules having non-identical amino acid sequences. Moieties useful in a multivalent conjugate of the invention that incorporates multiple homing molecules include, without limitation, phage, retroviruses, adenoviruses, adeno-associated viruses and other viruses, cells, liposomes, polymeric matrices, non-polymeric matrices or particles such as gold particles, microdevices and nanodevices, and nano-scale semiconductor materials.

A multivalent conjugate of the invention can contain, for example, a liposome or other polymeric matrix linked to at least two homing molecules that each selectively homes to tumor blood vessels and tumor cells and each specifically binds nucleolin. If desired, the liposome or other polymeric matrix can be linked to at least ten or at least 100 of such homing molecules. Homing molecules useful in such a multivalent conjugate can independently include, for example, the amino acid sequence SEQ ID NO: 9 or a conservative variant or peptidomimetic of this sequence. Liposomes consisting, for example, of phospholipids or other lipids, are nontoxic, physiologically acceptable and metabolizable carriers that are relatively simple to make and administer (Gregoriadis, *Liposome Technology*, Vol. 1 (CRC Press, Boca Raton, Fla. (1984)). The liposome or other polymeric matrix additionally can include another component if desired, such as a therapeutic agent, anti-angiogenic agent or cytotoxic agent.

A conjugate of the invention includes a therapeutic moiety linked to a homing molecule that selectively homes to tumor blood vessels and tumor cells and that specifically binds nucleolin. As used herein, the term "therapeutic moiety" is used broadly to mean a physical, chemical, or biological material that can be linked to a homing molecule and that alters biological activity in a normal or pathologic tissue upon administration. A therapeutic moiety, therefore, is potentially useful for the treatment of disease conditions. A therapeutic moiety can be any natural or nonnatural material including a biological material, such as a cell or phage; an organic chemical, such as a small molecule; a radionuclide; a nucleic acid molecule or oligonucleotide; a polypeptide; or a peptide or peptidomimetic. Therapeutic moieties useful in the invention include, without limitation, cancer chemotherapeutic agents; cytotoxic agents; pro-apoptotic agents; and anti-angiogenic agents. A therapeutic moiety useful in the invention can be expressed on, contained in, or linked to any of the following: phage or other virus, cell, liposome, polymeric or non-polymeric matrix, gold or other particle, or a microdevice, nanodevice, or nano-scale semiconductor material. These and other materials known in the art can be components of the conjugates of the invention.

A therapeutic moiety useful in a conjugate of the invention can be, for example, an anti-angiogenic agent. As used herein, the term "anti-angiogenic agent" means a molecule that reduces or inhibits angiogenesis. An anti-angiogenic agent useful in the conjugates and methods of the invention can be, for example, an inhibitor or neutralizing antibody that reduces the expression or signaling of an angiogenic factor such as vascular endothelial growth factor (VEGF), which is a major inducer of angiogenesis in normal and pathological conditions, and is essential in embryonic vasculogenesis. The biological effects of VEGF include stimulation of endothelial cell proliferation, survival, migration and tube formation, and regulation of vascular permeability. An anti-angiogenic agent also can inhibit another angiogenic factor such as a member of the fibroblast growth factor (FGF) family such as FGF-1 (acidic), FGF-2 (basic), FGF-4 or FGF-5 (Slavin et al., *Cell Biol. Int.* 19:431-444 (1995); Folkman and Shing, *J. Biol. Chem.* 267:10931-10934 (1992)) or angiopoietin-1, a factor that signals through the endothelial cell-specific Tie2 receptor tyrosine kinase (Davis et al., *Cell* 87:1161-1169 (1996); and Suri et al., *Cell* 87:1171-1180 (1996)), or the receptor of one of these angiogenic factors. It is understood that a variety of mechanisms can act to inhibit activity of an angiogenic factor including, without limitation, direct inhibition of receptor binding or of secretion of the angiogenic factor into the extracellular space, and inhibition of signaling, expression or function of the angiogenic factor.

A variety of anti-angiogenic agents useful in the invention are known in the art and can be prepared by routine methods. See, for example, Hagedorn and Bikfalvi, *Crit. Rev. Oncol. Hematol.* 34:89-110 (2000) and Kirsch et al., *J. Neurooncol.* 50:149-163 (2000). Anti-angiogenic agents include, without limitation, small molecules; proteins such as angiogenic factors and receptors, transcription factors, and antibodies and antigen-binding fragments thereof; peptides and peptidomimetics; and nucleic acid molecules including ribozymes, antisense oligonucleotides, and nucleic acid molecules encoding, for example, dominant negative angiogenic factors and receptors, transcription factors, and antibodies and antigen-binding fragments thereof. Exemplary anti-angiogenic agents useful in the conjugates and methods of the invention include, yet are not limited to, angiostatin, endostatin, metastatin and 2ME2 (EntreMed; Rockville, Md.); anti-VEGF antibodies such as Avastin (Genentech; South San Francisco, Calif.); VEGFR-2 inhibitors such as the small molecules SU5416 and SU6668, (SUGEN; South San Francisco, Calif.); heparin-binding fragments of fibronectin; modified forms of antithrombin; collagenase inhibitors; basement membrane turnover inhibitors; angiostatic steroids; platelet factor 4, and fragments and peptides, thereof; thrombospondin, and fragments and peptides thereof; and doxorubicin (O'Reilly et al., *Cell* 79:315-328 (1994)); O'Reilly et al., *Cell* 88: 277-285 (1997); Homandberg et al., *Am. J. Path.* 120:327-332 (1985); *Biochim. Biophys. Acta* 874:61-71 (1986); and O'Reilly et al., *Science* 285:1926-1928 (1999)). It is understood that these as well as other anti-angiogenic agents known in the art or that can be prepared by routine methods are encompassed by the term "anti-angiogenic agent" and can be used in the various conjugates and methods of the invention.

A therapeutic moiety useful in a conjugate of the invention can be, for example, a cytotoxic agent. As used herein, the term "cytotoxic agent" refers to any molecule that results in cell death by any mechanism. Exemplary cytotoxic agents useful in a conjugate of the invention encompass, without limitation, taxanes such as docetaxel; anthracyclins such as doxorubicin; alkylating agents; vinca alkaloids; anti-metabolites; platinum agents such as cisplatin or carboplatin; steroids such as methotrexate; antibiotics such as adriamycin; antimicrobial peptides, described herein below; and other cancer chemotherapeutic agents, which are chemical agents that inhibit the proliferation, growth, life-span or metastatic activity of cancer cells.

Taxanes are cytotoxic agents useful in a conjugate of the invention. Useful taxanes include, without limitation, docetaxel (Taxotere; Aventis Pharmaceuticals, Inc.; Parsippany, N.J.) and paclitaxel (Taxol; Bristol-Myers Squibb; Princeton, N.J.). See, for example, Chan et al., *J. Clin. Oncol.* 17:2341-2354 (1999), and Paridaens et al., *J. Clin. Oncol.* 18:724 (2000).

A cytotoxic agent useful in a conjugate of the invention also can be an anthracyclin such as doxorubicin, idarubicin or daunorubicin. Doxorubicin is a commonly used cancer chemotherapeutic agent (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity, which can contribute to its effectiveness in treating cancer (Folkman, supra, 1997; Steiner, In "Angiogenesis: Key principles-Science, technology and medicine," pp. 449-454 (eds. Steiner et al.; Birkhauser Verlag, 1992)).

An alkylating agent such as melphalan or chlorambucil also can be a cytotoxic agent useful in a conjugate of the invention. Similarly, vinca alkaloids such as vindesine, vinblastine or vinorelbine; or antimetabolites such as 5-fluorouracil, 5-fluorouridine or a derivative thereof are cytotoxic agents that can be linked to a homing molecule in a conjugate of the invention.

Cytotoxic agents useful in the conjugates of the invention also include platinum agents. Such a platinum agent can be, for example, cisplatin or carboplatin as described, for example, in Crown, *Seminars in Oncol.* 28:28-37 (2001). Other cytotoxic agents useful in a conjugate of the invention include, without limitation, methotrexate, mitomycin-C, adriamycin, ifosfamide and ansamycins.

A cytotoxic agent also can be, for example, an antimicrobial peptide. In one embodiment, the invention provides a conjugate in which a homing molecule that selectively homes to tumor blood vessels and tumor cells and that specifically binds nucleolin is linked to an antimicrobial peptide, where the conjugate is selectively internalized by tumor blood vessels and tumor cells and exhibits a high toxicity to the tumor blood vessels and tumor cells, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide, for example, can kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., supra, 1996; Blondelle and Houghten, supra, 1992). An antimicrobial peptide also can be, for example, a β-strand/sheet-forming peptide as described in Mancheno et al., *J. Peptide Res.* 51:142-148 (1998).

An antimicrobial peptide can be a naturally occurring or synthetic peptide. Naturally occurring antimicrobial peptides have been isolated from biological sources such as bacteria, insects, amphibians, and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274:151-155 (1990); and Blondelle and Houghten in Bristol (Ed.), *Annual Reports in Medicinal Chemistry* pages 159-168 Academic Press, San Diego). As discussed further below, an antimicrobial peptide also can be an analog of a natural peptide, especially one that retains or enhances amphipathicity.

An antimicrobial peptide incorporated within a conjugate of the invention has low mammalian cell toxicity when not linked to a tumor homing molecule. Mammalian cell toxicity readily can be assessed using routine assays. For example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 μM for lytic activity, preferably concentrations greater than 200, 300, 500 or 1000 μM.

In one embodiment, the invention provides a conjugate in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling or another assay well known in the art. $_D$(KLAKLAK)$_2$ (SEQ ID NO: 14), for example, is an antimicrobial peptide which induces marked mitochondrial swelling at a concentration of 10 μM, significantly less than the concentration required to kill eukaryotic cells. An antimicrobial peptide that induces significant mitochondrial swelling at, for example, 50 μM, 40 μM, 30 μM, 20 μM, 10 μM, or less, is considered a peptide that promotes disruption of mitochondrial membranes.

An antimicrobial peptide portion can include, for example, the sequence (KLAKLAK)$_2$ (SEQ ID NO: 14), (KLAKKLA)$_2$ (SEQ ID NO: 15), (KAAKKAA)$_2$ (SEQ ID NO: 16), or (KLGKKLG)$_3$ (SEQ ID NO: 17), and, in one embodiment, includes the sequence $_D$(KLAKLAK)$_2$(SEQ. ID NO: 14. A conjugate of the invention, which contains a homing molecule that selectively homes to tumor blood vessels and tumor cells linked to an antimicrobial peptide, can have, for example, the sequence KDEPQRRSARLSAKPA-PPKPEPKPKKAPAKK -GG-$_D$(KLAKLAK)$_2$ (SEQ ID NO: 21).

Antimicrobial peptides generally have random coil conformations in dilute aqueous solutions, yet high levels of helicity can be induced by helix-promoting solvents and amphipathic media such as micelles, synthetic bilayers or cell membranes.

α-Helical structures are well known in the art, with an ideal α-helix characterized by having 3.6 residues per turn and a translation of 1.5 Å per residue (5.4 Å per turn; see Creighton, *Proteins: Structures and Molecular Properties* W.H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., *Biochim. Biophys. Acta* 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., *Biopolymers* 37:105-122 (1995)). Synthetic, antimicrobial peptides having an amphipathic α-helical structure are known in the art, for example, as described in U.S. Pat. No. 5,789,542 to McLaughlin and Becker.

Effective cytotoxic agents include those that target DNA, for example, alkylating agents, agents that intercalate into DNA, and agents which result in double-stranded DNA breaks. Exemplary DNA-targeted drugs include, without limitation, cyclophosphamide, melphalan, mitomycin C, bizelesin, cisplatin, doxorubicin, etoposide, mitoxantrone, SN-38, Et-743, actinomycin D, bleomycin, TLK286 and SGN-15 (Hurley, supra, 2002).

A therapeutic moiety for treatment of breast cancer or another hormonally-dependent cancer also can be an agent that antagonizes the effect of estrogen, such as a selective estrogen receptor modulator or an anti-estrogen. The selective estrogen receptor modulator, tamoxifen, is a cancer chemotherapeutic agent that can be used in a conjugate of the invention for treatment of breast cancer (Fisher et al., *J. Natl. Cancer Instit.* 90:1371-1388 (1998)).

A therapeutic moiety useful in a conjugate of the invention also can be an antibody such as a humanized monoclonal antibody. As an example, the anti-epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (Burris et al., supra, 2001; White et al., *Annu. Rev. Med.* 52:125-141 (2001)).

It is understood by one skilled in the art of medicinal oncology that these and other agents are useful therapeutic moieties, which can be used separately or together in the conjugates and methods of the invention. It further is understood that a conjugate of the invention can contain one or more of such therapeutic moieties and that additional components can be included as part of the conjugate, if desired. As an example, in some cases it can be desirable to utilize an oligopeptide spacer between the homing molecule and the therapeutic agent (Fitzpatrick and Garnett, *Anticancer Drug Des.* 10:1-9 (1995)).

A conjugate of the invention also can include a detectable label. As used herein, the term "detectable label" refers to any molecule which can be administered in vivo and subsequently detected. Exemplary detectable labels useful in the conjugates and methods of the invention include radiolabels and fluorescent molecules. Exemplary radionuclides include indium-111, technetium-99, carbon-11, and carbon-13. Fluorescent molecules include, without limitation, fluorescein, allophycocyanin, phycoerythrin, rhodamine, and Texas red.

The present invention also provides methods of directing a therapeutic moiety to tumor blood vessels and tumor cells in a subject by administering to the subject a conjugate which contains a therapeutic moiety linked to a homing molecule that selectively homes to tumor blood vessels and tumor cells and that specifically binds nucleolin, thereby directing the therapeutic moiety to tumor blood vessels and tumor cells. In one embodiment, the homing molecule is not an antibody or antigen-binding fragment thereof. In other embodiments, the peptide or peptidomimetic portion of the conjugate has a length of at most 200 residues, or a length of at most 50 residues.

A variety of homing molecules are useful in the methods of the invention including homing peptides and peptidomimetics. A method of directing a therapeutic moiety to tumor blood vessels and tumor cells in a subject can be practiced, for example, using a homing peptide or peptidomimetic that contains the amino acid sequence SEQ ID NO: 9, or a conservative variant or peptidomimetic of this sequence. In one embodiment, such a homing peptide or peptidomimetic includes the amino acid sequence SEQ ID NO: 9, or a peptidomimetic thereof. A method of directing a therapeutic moiety to tumor blood vessels and tumor cells in a subject also can be practiced, for example, with a homing peptide or peptidomimetic which contains the amino acid sequence SEQ ID NO: 11, or a conservative variant or peptidomimetic of this sequence. In one embodiment, the method is practiced with a conjugate containing a homing peptide or peptidomimetic that includes the amino acid sequence SEQ ID NO: 11 or a peptidomimetic thereof.

A variety of therapeutic moieties can be directed to tumor blood vessels and tumor cells in a subject according to a method of the invention. Such moieties encompass, without limitation, anti-angiogenic agents and cytotoxic agents, including cytotoxic agents that target a DNA-associated process such as alkylating agents, anti-tumor antibiotics and sequence-selective cytotoxic agents. In particular embodiments, a method of the invention relies on one of the following cytotoxic agents that target a DNA-associated process: cyclophosphamide, melphalan, mitomycin C, bizelesin, cisplatin, doxorubicin, etoposide, mitoxantrone, SN-38, Et-743, actinomycin D, bleomycin or TLK286.

The present invention also provides a method of imaging tumors and tumor vasculature in a subject by administering to the subject a conjugate containing a detectable label linked to a homing molecule that selectively homes to tumor blood vessels and tumor cells and that specifically binds nucleolin; and detecting the conjugate, thereby imaging tumors and tumor vasculature. A homing molecule useful in an imaging method of the invention can be, for example, a homing peptide or peptidomimetic such as a homing peptide or peptidomimetic that contains the amino acid sequence SEQ ID NO: 9 or a conservative variant or peptidomimetic of this sequence. Any of a variety of detectable labels are useful in the imaging methods of the invention, including fluorescent labels and radionuclides such as indium-111, technetium-99, carbon-11, and carbon-13.

The methods of the invention for imaging tumors and tumor vasculature can be useful for detecting the presence of blood vessels associated with a variety of tumors. Following administration of a conjugate of the invention containing a detectable label, tumor blood vessels are visualized. If the image is positive for the presence of such tumor vessels, the tumor can be evaluated for size and quantity of vascular infiltration. These results provide valuable information to the clinician with regard to the stage of development of the cancer and the presence or probability of metastasis.

In a method of imaging tumors and tumor vasculature, the conjugate administered contains a detectable label that allows detection or visualization of tumor blood vessels and tumor cells, for example, of leukemias or breast cancers. For in vivo diagnostic imaging of such cancers, a homing molecule is linked to a detectable label that, upon administration to the subject, is detectable external to the subject. Such a detectable label can be, for example, a gamma ray emitting radionuclide such as indium-113, indium-115 or technetium-99; following administration to a subject, the conjugate can be visualized using a solid scintillation detector.

The present invention also provides a method of reducing the number of tumor blood vessels in a subject by administering to the subject a conjugate which contains a cytotoxic agent linked to a homing molecule that selectively homes to tumor blood vessels and tumor cells and that specifically binds nucleolin, thereby reducing the number of tumor blood vessels in the subject. The peptide or peptidomimetic portion of the conjugate can have, for example, a length of at most 200 residues, or a length of at most 50 residues. In one embodiment, a method of the invention is practiced with a conjugate containing a homing peptide or peptidomimetic. In a further embodiment, a method of the invention is practiced with a conjugate containing a homing peptide or peptidomimetic that includes the amino acid sequence SEQ ID NO: 9, or a conservative variant or peptidomimetic of this sequence. Any of the therapeutic moieties described above, such as anti-angiogenic agents, cytotoxic agents and cytotoxic agents that target a DNA-associated process, as well as additional moieties disclosed herein or known in the art, can be used to reduce the number of tumor blood vessels according to a method of the invention.

Also provided herein is a method of treating cancer in a subject by administering to the subject a conjugate which contains a therapeutic moiety linked to a homing molecule that selectively homes to tumor blood vessels and tumor cells and that specifically binds nucleolin. In particular embodiments, the peptide or peptidomimetic portion of the conjugate has a length of at most 200 residues, or a length of at most 50 residues. In other embodiments, a method of the invention is practiced with a conjugate containing a homing peptide or peptidomimetic such as a homing peptide or peptidomimetic that includes the amino acid sequence SEQ ID NO: 9, or a conservative variant or peptidomimetic of this sequence. It is understood that, in a method of the invention for treating cancer in a subject, any of a variety of therapeutic moieties can be useful, including but not limited to, anti-angiogenic agents; cytotoxic agents; and cyclophosphamide, melphalan, mitomycin C, bizelesin, cisplatin, doxorubicin, etoposide, mitoxantrone, SN-38, Et-743, actinomycin D, bleomycin, TLK286 and other cytotoxic agents that target a DNA-associated process.

It is understood that a variety of routes of administration are useful in the methods of the invention. Such routes encompass systemic and local administration and include, without limitation, oral administration, intravenous injection, intraperitoneal injection, intramuscular injection, subcutaneous injection, transdermal diffusion or electrophoresis, local injection; extended release delivery devices, including locally implanted extended release devices such as bioerodible or reservoir-based implants.

The present invention further provides a method of isolating progenitor cells from a heterogeneous mixture of cells by contacting the heterogenous mixture of cells with a homing molecule that selectively homes to tumor blood vessels and tumor cells and specifically binds nucleolin under conditions suitable for specific binding of the homing molecule to the progenitor cells; and separating cells that bind the homing molecule from non-binding cells, thereby isolating progenitor cells from the heterogenous mixture of cells. The heterogeneous mixture of cells can be, for example, primary tissue such as primary bone marrow.

In one embodiment, the homing molecule used to isolate progenitor cells according to a method of the invention is a homing peptide or peptidomimetic. In a further embodiment, the method is practiced with a homing peptide or peptidomimetic containing the amino acid sequence SEQ ID NO: 9 or a conservative variant or peptidomimetic thereof. In another embodiment, the method is practiced with a homing peptide or peptidomimetic containing the amino acid sequence SEQ ID NO: 11 or a conservative variant or peptidomimetic thereof. Homing peptides and peptidomimetics useful in isolating progenitor cells can have a variety of lengths, including, without limitation, a length of less than 85 residues, a length of less than 50 residues, or a length of less than 35 residues.

A method of the invention for isolating progenitor cells can be practiced, if desired, with a homing molecule attached to a support. A method of the invention also can be practiced, for example, with a homing molecule linked to a fluorescent label. In one embodiment, the separation step includes fluorescence activated cell sorting (FACS). In further embodiments, progenitor cells are isolated using a homing peptide or peptidomimetic containing the amino acid sequence SEQ ID NO: 9 or the amino acid sequence SEQ ID NO: 11, or a conservative variant or peptidomimetic of one of these sequences, linked to a fluorescent label.

The following examples are intended to illustrate but not limit the present invention.

EXAMPLE I

In Vivo Homing of a Fragment of HMGN2

This example demonstrates that an amino-terminal fragment of HMGN2 selectively homes to tumor blood vessels and tumor cells in vivo.

Hematopoietic and endothelial precursors originate from a common precursor, hemangioblasts. Based on the shared phenotypic characteristics of hematopoietic and endothelial precursors, a phage screening procedure was devised to select cDNA clones that bind an epitope shared by both primitive bone marrow cells and angiogenic endothelial cells. The screening procedure included an ex vivo primary selection on lineage-depleted murine bone marrow cells to select for binding to endothelial progenitor cells and a further selection for homing to HL-60 xenograft tumors in vivo.

Figure 1:
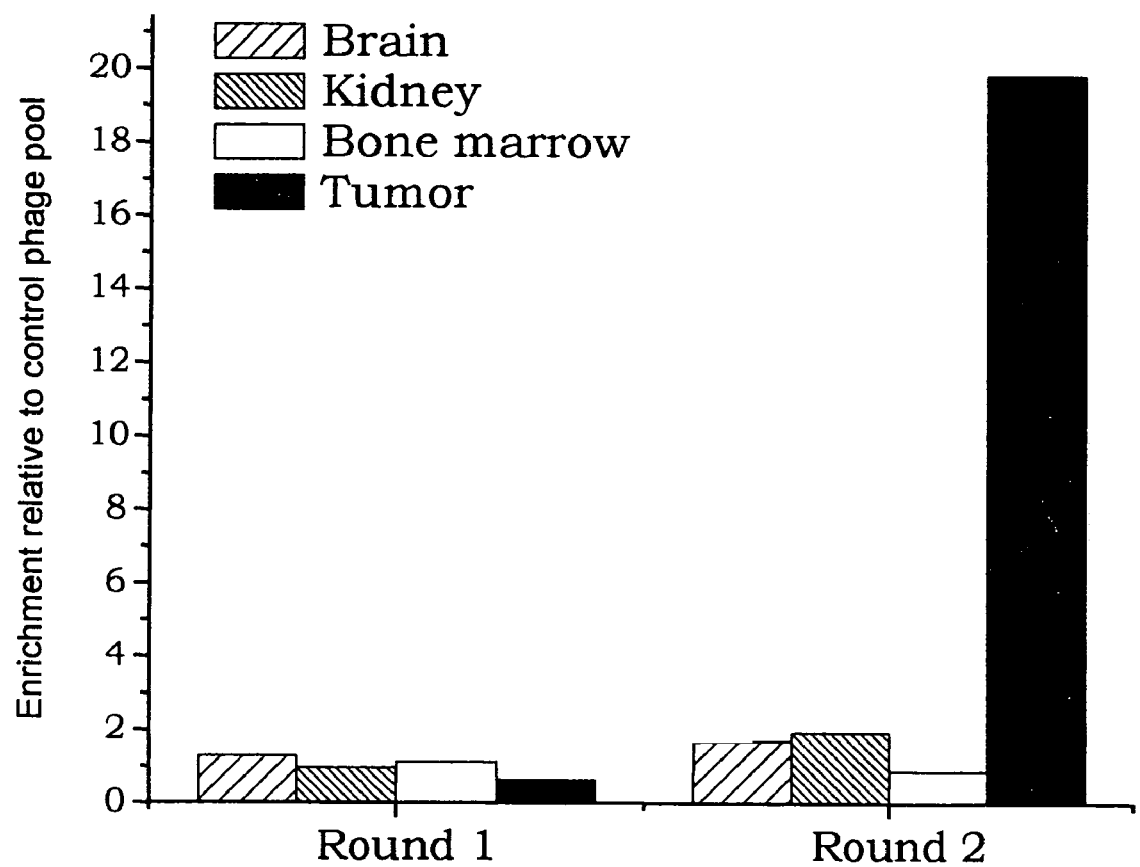
FIG. 1 shows phage enrichment in vivo. The Y-axis shows fold enrichment of selected phage relative to the unselected cDNA phage library pool.

After two rounds of pre-selection on lineage-depleted murine bone marrow cells, the resulting phage pool was injected into the tail vein of nude mice bearing HL-60 tumors. After 10 minutes of circulation, the mice were perfused through the heart, and the phage rescued from various organs, amplified, and used for subsequent rounds of selection. As shown in FIG. 1, the selected phage pool exhibited 20-fold enrichment for tumor homing relative to the unselected library after two rounds of in vivo selection. Sequencing analysis showed that the predominant cDNA in the selected pool was a 270-bp clone (SEQ ID NO: 5) that contained an open reading frame encoding the first 73 amino-terminal residues of human HMGN2 as well as 51 bp of 5' non-coding sequence (FIG. 2A). As further shown in FIG. 2A, additional HMGN2 clones (SEQ ID NOS: 1 through 4) also were isolated from the phage pool; all the HMGN2 clones shared a common sequence corresponding to exons 3 and 4 in the HMGN2 sequence (see FIG. 2A).

An independent screening strategy also resulted in isolation of the same HMGN2 cDNA clone, SEQ ID NO: 5. In this second strategy, an initial pre-selection was performed by assaying for in vitro binding to murine bone marrow cells positive for the progenitor cell marker, CD34, followed by in vivo selection in nude mice bearing MDA-MB-435 human breast cancer xenografts.

Purified phage bearing the HMGN2 fragment SEQ ID NO: 5 homed to HL-60 tumors in vivo to about the same extent as the selected pool. The purified phage displaying SEQ ID NO: 5 also accumulated in the kidneys if the number of injected phage was small ($1 \times 10^9$ plaque forming units (pfu)). In contrast, homing to tumors was observed using either $1 \times 10^9$ pfu or $1 \times 10^{12}$ pfu injected phage.

As expected, phage bearing the HMGN2 fragment SEQ ID NO: 5 also exhibited a preference for binding tumor cells in vitro. In particular, about 1000 times more SEQ ID NO: 5-displaying phage than non-recombinant T7 phage bound to cultured HL-60 or MDA-MB-435 cells in vitro. Similarly, SEQ ID NO: 5-displaying also bound cell suspensions prepared from HL-60 tumors with a 1000-fold specificity relative to control T7 phage. These results indicate that the HMGN2 fragment SEQ ID NO: 5 is sufficient for selective homing to tumors of different types.

Cell lines were maintained and xenograft tumors were established as follows. Human myeloid leukemia HL-60 (ATTC) and MDA-MB-435 human breast carcinoma cell lines were grown in RPMI-1640 media supplemented with 10% fetal bovine serum (Arap et al., *Science*, 279:377-380 (1998)). To establish xenograft tumors, 2 to 3-month old nude mice (Harlan Sprague Dawley; San Diego, Calif.) were injected subcutaneously with $10^6$ exponentially growing tumor cells in 200 µl culture media. HL-60 and MDA-MB-435 xenograft bearing animals were used in experiments within 3-5 weeks or 8-10 weeks, respectively, of the time of the injection.

cDNA synthesis, cloning, and phage packaging and amplification were performed essentially as follows. Phage cDNA libraries were prepared using mRNA purified from normal (human bone marrow, brain or mouse embryo) or malignant (liver, lung, breast, and colon carcinoma) tissues (BD Biosciences Clontech; Palo Alto, Calif.) and from mouse spleen and bone marrow (Oligotex Direct mRNA kit; Qiagen; Valencia, Calif.). cDNA synthesis was performed with random primers; cDNAs were cloned into the T7Select 10-3b vector; and phage were packaged and amplified according to the manufacturer's instructions (Novagen; Madison, Wis.). cDNA libraries were pooled for the phage screening.

Murine bone marrow progenitor cells were isolated and depleted of cells bearing several lineage-specific markers essentially as follows. Mouse bone marrow was obtained by flushing femoral and tibial bones with 3 ml cold media (DMEM supplemented with 10% FBS). Bone marrow subsequently was depleted of cells expressing common lineage-specific markers by using the StemSep Murine Kit (StemCell Technologies; Vancouver, Canada) with antibodies recognizing the following antigens coupled to paramagnetic beads: mouse CD5 (clone Ly-1); myeloid differentiation antigen (Gr-1); CD45R (B220); erythroid cells (TER119); CD11b (Mac-1); and neutrophils (7-4; StemCell Technologies). After depletion of cells bearing lineage-specific markers, the remaining megakaryocytes were removed by filtering through a 30 µm nylon mesh filter (Miltenyi Biotech; Auburn, Calif.).

Ex vivo and in vivo selections were performed as described (Rajotte et al., *Journal of Clinical Investigation* 102:430-437 (1998); Hoffman, et al., in *Phage Display: A Practical Approach*, eds. Clarkson, T. & Lowman, H., Oxford University Press, Oxford, UK (2002), In press; Laakkonen et al., *Nature Medicine* In revision, 28-30 (2002)). Briefly, $1 \times 10^9$ pfu of phage library were incubated with target cells overnight at 4° C. After unbound phage were removed by extensive washing, phage bound to cells were rescued, amplified, and used for the subsequent round of selection. After two rounds of in vitro selection, the phage pool was subjected to in vivo selection by injecting the pool ($1 \times 10^9$ pfu) into the tail vein of a nude mouse bearing an HL-60 xenograft tumor. After two rounds of in vivo selection, 96 phage clones were selected from the pool of tumor-homing phage. Protein-encoding inserts were sequenced by standard methods.

EXAMPLE II

Delineation of the HMGN2 Tumor Cell-Binding Domain

This example describes localization of the HMGN2 domain responsible for tumor cell binding and in vivo homing activity.

A. Identification of an HMGN2-Derived Peptide Sequence Sufficient for Tumor Cell Binding and in Vivo Homing Activity.

Phage displaying a set of sequences corresponding to fragments of the amino-terminal portion of HMGN2 (SEQ ID NO: 5) were constructed to localize the region responsible for cell binding and in vivo homing. Fragments were designed to follow the exon/intron boundaries of the HMGN2 gene. Inserts encoding the indicated fragments were amplified from the full length HMGN2 phage clone by PCR, purified, digested and directionally cloned into the T7 415-1 and 10-3 vectors. Phage were packaged, amplified and sequenced according to the manufacturer's instructions. Phage preparations were then tested for binding to primary cells obtained from HL-60 xenograft tumors. After a 1 hour incubation at 4° C., cells were washed, and bound phage quantified. As shown in FIG. 2B, when phage bearing fragments SEQ ID NO: 7, 8, 9 and 10 were tested for tumor binding activity as compared to non-recombinant phage, only the 31-amino acid fragment encoded by exons 3 and 4 (SEQ ID NO: 9), which corresponds to the nucleosomal binding domain of HMGN2, demonstrated substantial tumor cell binding (FIG. 2B). Furthermore, phage displaying the N-terminal portion of the active fragment SEQ ID NO: 9, which corresponds to exon 3 of the HMGN2 gene, were prepared. These phage expressing the sequence PQRRSARLSA (SEQ ID NO: 11) bound to tumor cells 90-fold more than non-recombinant phage.

The phage binding assay was performed essentially as follows. Attachment of phage to cells was quantified by incubating $1 \times 10^8$ pfu of phage displaying SEQ ID NO: 9 for 60 minutes with $1 \times 10^6$ HL-60 cells at 4° C. in Tris-buffered saline with 1 mM $Ca^{+2}$ and 1 mM $MgCl_2$. Bound phage were rescued after four washes with phosphate-buffered saline by adding 1 ml of bacteria for 7 minutes at room temperature. Bound phage were quantified by plating and counting pfu.

B. Specificity of Active Peptide Binding

Binding of SEQ ID NO: 9-displaying phage to tumor cells was inhibited by free SEQ ID NO: 9 peptide in a dose dependent fashion. Complete inhibition was achieved with 100 µM free peptide SEQ ID NO: 9, indicating that phage binding was specific. In contrast, background binding of non-recombinant phage was unaffected by free peptide. Specificity of cell binding by peptide SEQ ID NO: 9 was further confirmed by comparing HL-60 cell binding of phage expressing the HMGN2 exon 3 sequence PQRRSARLSA (SEQ ID NO: 11) to binding with phage expressing the homologous HMGN1 exon 3 sequence PKRRSARLSA (SEQ ID NO: 12). The HMGN1 phage expressing SEQ ID NO: 12 bound 90% less than the HMGN2 phage expressing SEQ ID NO: 11, indicating that the single amino acid change from glutamine to lysine substantially alters cell binding specificity of the homing fragment.

These results indicate that binding of SEQ ID NO: 9-displaying phage is due to the specific binding activity of SEQ ID NO: 9.

EXAMPLE III

Tissue and Sub-Cellular Localization of HMGN2 Peptide SEQ ID NO: 9

This example demonstrates that peptide SEQ ID NO: 9 accumulates in tumor cells and cells lining the blood vessels upon intravenous administration.

A. Histological Analysis of HMGN2 Peptide Homing

To study peptide localization, fluorescein-conjugated SEQ ID NO: 9 or ARALPSQRSR (SEQ ID NO: 13) was injected into the tail vein of mice bearing HL-60 or MDA-MB-435 xenografts. Peptide injection was followed 10 minutes later by injection of biotinylated tomato lectin, a marker of the vasculature. After another five minutes, mice were perfused through the heart with fixative solution, and the organs dissected, sectioned and stained with streptavidin-AlexaFluor 594. Slides were counter-stained with DAPI and examined under an inverted fluorescent microscope. As shown in FIG. 3A, strong fluorescence was present in tumor tissue, whereas little or no specific fluorescence was detected in normal brain, liver or spleen. See, for example, FIG. 3B, which shows immunofluorescence of brain tissue. HMGN2 peptide SEQ ID NO: 9 also was present in a small population of cells in the skin and the gut, which were not associated with the vasculature and which may represent progenitor cells (see FIGS. 3C and D). In addition, diffuse fluorescence accumulated in proximal tubules of kidneys following injection with peptide SEQ ID NO: 9 or fluorescein-labeled scrambled exon 3 peptide (ARALPSQRSR; SEQ ID NO: 13), indicating that kidney staining was due to non-specific uptake of peptide or fluorescein from the glomerular filtrate. The control peptide ARALPSQRSR (SEQ ID NO: 13) was essentially undetectable in other tissues, including the HL-60 tumors, as shown in FIG. 3E.

Within the HL-60 leukemia tumor tissue, SEQ ID NO: 9 localized to tumor cells and cells lining tumor blood vessels. As shown in FIGS. 3A and G-J, fluorescence predominantly localized to nuclei, with most of the tumor cells containing fluorescence positioned close to blood vessels. Fluorescein-conjugated peptide SEQ ID NO: 9 also accumulated in endothelial cells and tumor cells in mice expressing MDA-MB-435 breast cancer xenografts. In some microscopic fields, SEQ ID NO: 9 fluorescence essentially was limited to the endothelial cells, clearly illustrating the expression of peptide SEQ ID NO: 9 within endothelial cells and their nuclei (see FIG. 3F). Similar tumor localization was obtained when peptide SEQ ID NO: 9 was coupled to another fluorescent molecule, rhodamine. In sum, these results indicate that peptide SEQ ID NO: 9 selectively homes to tumors and tumor endothelial cells as well as a minor population of progenitor cell-like bone marrow cells and a small population of cells in normal skin and gut.

Peptides were synthesized with an automated peptide synthesizer by using standard solid-phase Fmoc chemistry (Atherton and Sheppard, *Solid-Phase Peptide Synthesis*, IRL, Oxford (1989)). Peptides were labeled with fluorescein via an amino-hexanoic acid spacer during peptide synthesis as described in Wender et al., *Proc. Nat. Acad. Sci. USA* 97: 13003-13008 (2000). The concentration of unlabeled peptide was determined by weighing and from absorbance at 230 nm (Ehresmann et al., *Analytical Biochemistry* 54:454-463 (1973)).

Histological analyses were performed as follows. Tissue distribution of homing ligands was examined by intravenously injecting fluorescein-coupled peptides (100 μl of 1 mM solution) into the tail vein of anesthesized mice bearing HL-60 xenografts prepared as described above. Blood vessels were visualized by intravenously injecting 200 μl of 0.5 μg/μl biotin-conjugated tomato lectin (Vector Laboratories; Burlingame, Calif.). Peptide was injected first, followed by lectin, and the injected materials were allowed to circulate for five minutes. The mouse, which remained anesthesized throughout the experiment, was perfused subsequently through the heart with 4% paraformaldehyde. Organs were removed and frozen in O.C.T. embedding medium (Tissue-Tek; Elkhart, Ind.). Biotin-conjugated lectin was detected with streptavidin-Alexa 594 (Molecular Probes; Eugene, Oreg.); the slides were mounted with Vectashield-DAPI (Vector Laboratories; Burlingame, Calif.), and examined under an inverted fluorescent microscope.

Figure 4:
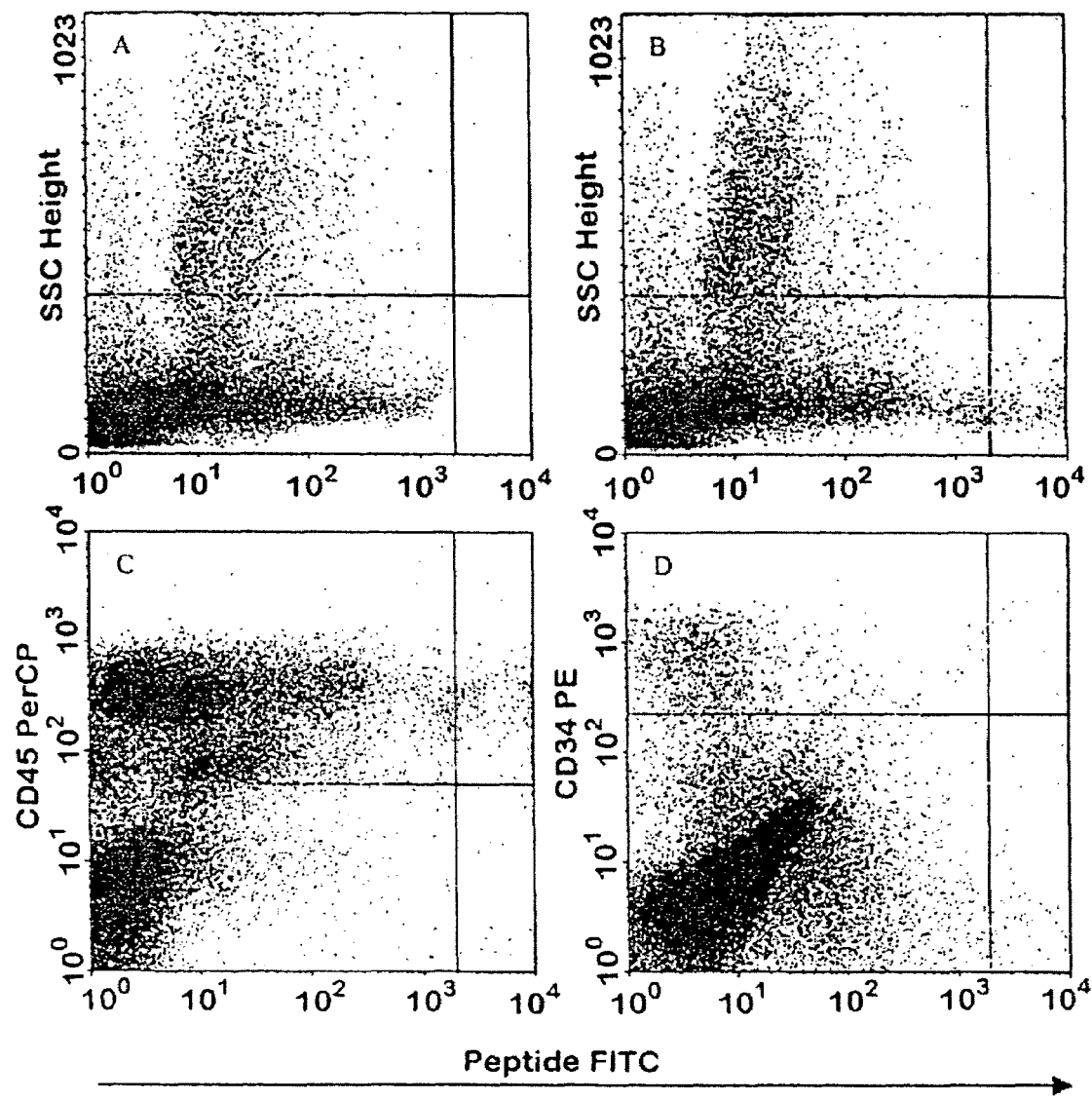
FIG. 4 shows a FACS profile of bone marrow cells labeled with fluorescent peptide SEQ ID NO: 9 and with antibodies against cell differentiation markers. (A) control peptide SEQ ID NO: 13 (number/percentage of cells in lower right quadrant: 1/0.0). (B) peptide SEQ ID NO: 9 (308/0.88). (C) SEQ ID NO: 9 vs. CD45 (77% CD45-positive). (D) SEQ ID NO: 9 vs. CD34 (75% CD34-negative).

B. Peptide SEQ ID NO: 9 Binds Cells in Human Bone Marrow with Progenitor Cell-Like Characteristics Fluorescein-labeled SEQ ID NO: 9 or control peptide SEQ ID NO: 13 (2 μM) were incubated with gradient-depleted bone marrow cells for one hour at 4° C. and analyzed in a flow cytometer. As shown in FIG. 4, peptide SEQ ID NO: 9 specifically bound to a small cell population in human bone marrow, representing about 0.3-0.8% of mononuclear cells. The SEQ ID NO: 9-positive cells were the size of lymphocytes, agranular, CD45-positive and mostly CD34-negative, a marker profile similar to that of the lineage-depleted murine bone marrow cells used in the in vitro phage selection. These results indicate that peptide SEQ ID NO: 9 binds a minor population of progenitor cell-like bone marrow cells.

Flow cytometry was performed as follows. Human bone marrow specimens represented excess material from samples collected for diagnostic purposes from adults with hematological malignancies following informed consent. A total of 2 ml of bone marrow was aspirated from the posterior iliac crest and stored in a citrate anticoagulant. Mononuclear cells were isolated by gradient centrifugation (Ficoll-Paque PLUS; Amersham Pharmacia Biotech; Uppsala, Sweden) and incubated in RPMI-1640 media supplemented with 10% FBS for two hours at 37° C. Cells subsequently were transferred to 4° C. and incubated with 1-2 μM fluorescein-conjugated peptide for 45 minutes before staining with PerCP- or PE-conjugated CD34 and CD45 antibodies (Beckton Dickinson Biosciences; San Jose, Calif.) for 30 minutes. Samples were analyzed with either a FACSCalibur or LSR flow cytometer (Beckton Dickinson Biosciences); 100,000 events were collected.

C. Rapid Nuclear Uptake of Peptide SEQ ID NO: 9 in Tumor Cells in Vitro

Cellular uptake and nuclear translocation of peptide SEQ ID NO: 9 were observed in cultured HL-60 cells and MDA- MB-435 cells in vitro. HL-60 or MDA-MB-435 cells were incubated with 1 µM fluorescein-labeled SEQ ID NO: 9 or control peptide SEQ ID NO: 13 at 370. After 30 minutes, cells were washed, fixed, stained with nuclear counter-stain (DAPI; blue), and imaged under a confocal or epifluorescent microscope. As shown in FIG. 5, peptide SEQ ID NO: 9 rapidly localized to the nucleus. The uptake of peptide SEQ ID NO: 9 did not occur efficiently at 4° C., indicating energy dependence. Furthermore, while the D-amino acid form of peptide SEQ ID NO: 9 also was internalized by MDA-MB-435 cells, albeit more slowly than the L-form, the D-form did not accumulate in the nucleus. These properties were reminiscent of the cellular uptake and nuclear translocation of highly basic peptides from Tat protein and certain homeobox proteins (Lindgren et al., *Trends in Pharmacological Sciences* 21:99-103 (2000); Schwarze et al., *Science* 285:1569-1572 (1999) and Gallouzi and Steitz, *Science* 294:1895-1901 (2001)).

In sum, these results demonstrate that peptide SEQ ID NO: 9 localizes to the nuclei of tumor cells upon internalization and further indicate that peptide SEQ ID NO: 9 and molecules that bind the same receptor can be useful for selectively targeting anti-cancer drugs to tumor vasculature.

EXAMPLE IV

Identification of Homing Molecules that Target the Receptor Bound by SEQ ID NO: 9

This example describes a routine binding competition assay for identification of homing molecules that bind the receptor bound by SEQ ID NO: 9.

Phage binding to cells is quantified by incubating $1 \times 10^8$ plaque forming units (pfu) of phage displaying SEQ ID NO: 9 for 60 minutes with $1 \times 10^6$ HL-60 cells at 4° C. in Tris buffered saline containing 1 mM $Ca^{+2}$ and $Mg^{+2}$. After four washes with phosphate-buffered saline, bound phage are rescued by addition of 1 ml bacteria for 7 minutes at room temperature. Bound phage are quantified by plating and counting pfu.

Inhibition of phage binding is determined by adding varying concentrations of a test molecule to the mixture of phage and HL-60 cells. Any significant inhibition of phage binding is an indication that the test molecule specifically binds to the same receptor as SEQ ID NO: 9 and is a homing molecule that selectively homes to tumor blood vessels and tumor cells.

EXAMPLE V

Isolation of Progenitor Cells

This example describes a procedure for purification of progenitor cells from bone marrow or another tissue source. Tumor cells or tumor blood vessels can be similarly purified using the appropriate tissue source.

Organs are removed from mice, rinsed in PBS, minced into approximately 1 mm squares, and digested in 10 ml collagenase A (1 mg/ml; SIGMA), DNase I (25 µg/ml; SIGMA), and Dispase II (2.4 U/ml; Roche) at 37° C. for 1.5 hours with continuous rotation. The cell suspension is filtered through 50 µm nylon mesh, centrifuged at 1000×g for five minutes, and washed once in PBS with 2% FCS and 5% rat serum. Cells are suspended and incubated with fluorescein-labeled peptide SEQ ID NO: 9 at 50 µg/ml, and mouse monoclonal anti-fluorescein antibody (Molecular Probes) for 15 minutes. The cell suspension is then centrifuged at 1000×g for five minutes. After resuspending the cell pellet in 90 µl buffer and 10 µl of anti-mouse IgG microbeads (Miltenyi Biotec), the mixture is rotated in the cold room for 15 minutes. After two washes with buffer, cells are resuspended in 0.5 ml buffer and applied to a MACS separation column on the MACS MultiStand. The column is washed with 1 ml of degassed buffer, and the cells are flushed out with the column plunger. The purity of the SEQ ID NO: 9-reactive cells is examined by incubating cells with fluorescein-coupled peptide SEQ ID NO: 9 at 25 µg/ml), and analyzing cells under a fluorescent microscope.

These results indicate that SEQ ID NO: 9-reactive cells can be purified by routine methods.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

EXAMPLE VI

Identification of the HMGN2 Target Molecule

This example demonstrates that cell surface nucleolin is a novel marker for tumor endothelium.

A. Affinity Chromatography Demonstrates that Nucleolin Binds Peptide SEQ ID NO: 9

As indicated above, cultured tumor cells, such as the human breast carcinoma cell line MDA-MB-435, bind the HMGN2-derived peptide, SEQ ID NO: 9, in vitro. As shown in FIG. 6A, affinity chromatography of MDA-MB-435 cell extracts revealed a major band at a molecular weight of 110 kDa and several bands in the 20 kDa range that bound to peptide SEQ ID NO: 9 but not to control peptide. Mass spectrometric analysis indicated that the 110 kDa band represents nucleolin. The 20 kDa range bands were identified as various histones.

Affinity chromatography with peptide SEQ ID NO: 9 and MDA-MB-435 detergent extracts was performed essentially as described in Christian et al., *J. Biol. CHem.* 276:48588-48595 (2001). Briefly, $6 \times 10^8$ MDA-MB-435 cells grown in RPMI 1640 medium with 10% fetal calf serum were pelleted and lysed in 60 ml of RIPA buffer (1% Triton X-100, 0.5% deoxycholic acid, 0.1% SDS, 10 mM Tris-HCl pH 7.6, 150 mM NaCl, and 1% Protease Inhibitor Cocktail for Mammalian Cells; SIGMA). The lysate was incubated with 20 ml of peptide SEQ ID NO: 9 or control peptide (APKDK-PAAVKERKKPAPKPRPQELRSKKAKPAPAS; SEQ ID NO:20) affinity matrix (2 mg of peptide covalently coupled to 1 ml of Affigel 10). Matrix beads were washed three times with IP-wash buffer (0.025% Triton X-100, 50 mM Tris-HCl pH 8.4, 150 mM NaCl, 1 mM $CaCl_2$, and 0.02% azide), two times with 25 mM Tris-HCl pH 8.4/250 mM NaCl, and eluted with 30 µl of SDS gel sample buffer. Affinity-purified proteins were reduced with 50 mM DTT before being separated on an 8-20% polyacrylamide gel and visualized by Colloidal Blue staining (Invitrogen; Carlsbad, Calif.). Bands that appeared in the peptide SEQ ID NO: 9 eluate, but not in control eluate, were cut out, digested with trypsin and analyzed by mass spectroscopy using matrix-assisted laser desorption ionization-time of flight analysis (Voyager DE-PRO, Applied Biosystems; Foster City, Calif.). Peptide samples were prepared using an alpha-cyano-4-hydroxycinnamic acid (HCCA)/nitrocellulose matrix.

Identification of the 110-kDa protein as nucleolin was confirmed by immunoblotting. A monoclonal antibody against nucleolin revealed a major 110-kDa band and a faint lower molecular size band in the peptide SEQ ID NO: 9-bound material (see FIG. 6B). These bands were not present in eluates from the control matrix. In the unfractionated sample ("extract"), anti-nucleolin antibody recognizes full-length nucleolin at 110 kDa, along with several faster-migrating bands, including one at 75 kDa. The faint bands in the material obtained by purification on SEQ ID NO: 9 matrix aligned with several of the lower molecular size bands detected by anti-nucleolin antibody in whole cell extracts, which are likely nucleolin fragments. These results show that the HMGN2-derived peptides such as peptide SEQ ID NO: 9 specifically bind nucleolin.

Immunoblot analysis was performed as follows. Cell extracts or affinity-purified material was separated by SDS-PAGE and transferred on nitrocellulose membrane for one hour at 100V. The membrane was blocked overnight at 4° C. in 5% milk powder in TBS-T (140 mM NaCl, 10 mM Tris-HCl pH 7.4, 0.05% Tween) and incubated with 10 mg/ml mouse monoclonal $IgG_1$ MS-3 anti-nucleolin antibody (Santa Cruz Biotechnology; Santa Cruz, Calif.) in TBS-T for one hour at room temperature. After extensive washing, the membrane was incubated with peroxidase coupled rabbit anti-mouse antibody; bound antibody was detected with enhanced chemiluminescence (ECL; Amersham) and exposure to Biomax MR (Kodak; Rochester, N.Y.).

B. Nucleolin is Expressed at the Cell Surface

Figure 7:
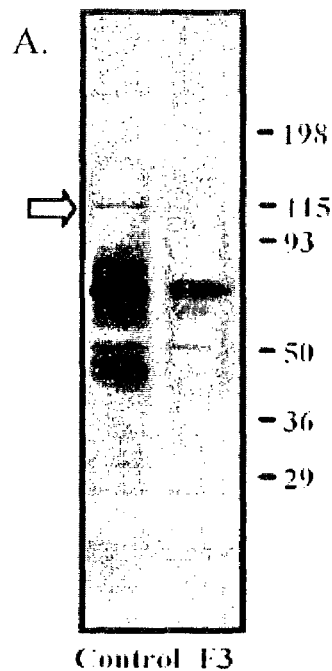
FIG. 7 shows cell surface expression of nucleolin in MDA-MB-435 breast cancer cells. (A) Peptide SEQ ID NO: 9 affinity chromatography ("F3") and control peptide chromatography of biotin-labeled proteins solubilized from cell surface-biotinylated MDA-MB-435 cells. (B) Fluorescence activated cell sorting (FACS) analysis of MDA-MB-435 cells and various antibodies. Propidium iodide-negative (living) cells were gated for the analysis.
Figure 7:
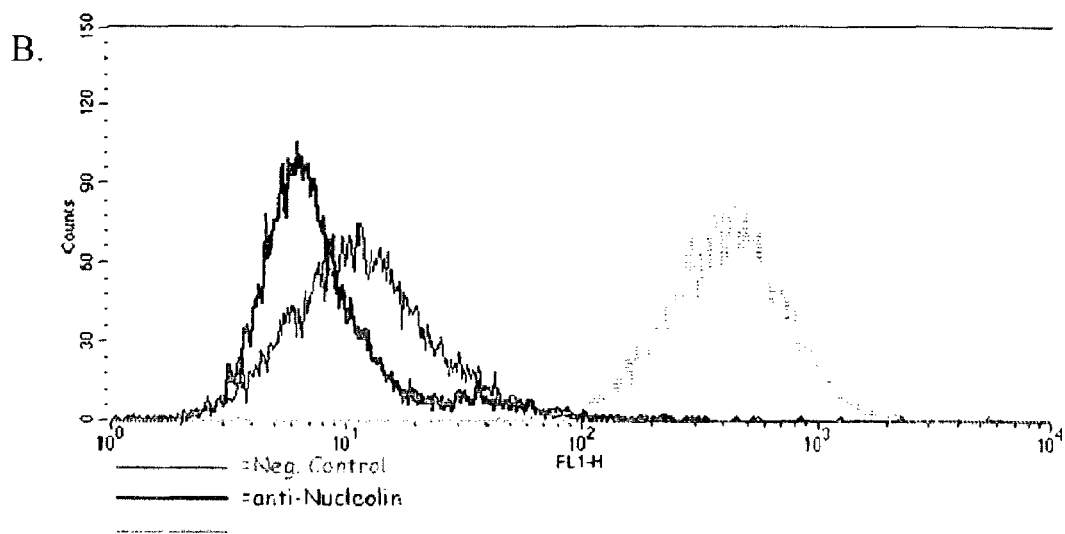

Nucleolin was originally described as a nuclear protein, although this protein has also been observed at the cell surface (Sinclair and O'Brien, *J. Biol. Chem.* 277:2876-2885 (2002); and Said et al., *J. Biol. Chem.* 277:37492-37502 (2002)). To determine if the SEQ ID NO: 9-binding nucleolin in MDA-MB-435 cells is expressed at the cell surface, MDA-MB-435 cells were biotinylated with a cell-impermeable biotin reagent, and the resulting cell extracts assayed for the ability to bind SEQ ID NO: 9. As shown in FIG. 7A, affinity purification on immobilized peptide SEQ ID NO: 9 identified two streptavidin-reactive bands at 110-kDa and 75-kDa that specifically bound to peptide SEQ ID NO: 9. The molecular weights of these bands were similar to the SEQ ID NO: 9-binding nucleolin bands detected with anti-nucleolin antibody. As expected, histones, which bound the SEQ ID NO: 9 peptide matrix in a cell extract, were not biotin-labeled in intact cells.

Cell surface biotinylation experiments were performed essentially as follows. MDA-MB-435 cells ($5 \times 10^6$ cells) were washed three times with cold phosphate-buffered saline on a cell culture plate and incubated with biotinylation buffer (20 mM HEPES, pH 7.45, 5 mM KCl, 130 mM NaCl, 0.8 mM $MgCl_2$, 1 mM $CaCl_2$, 0.5 mg/ml EZ link Sulfo-NHS-Biotin; Pierce) for one hour at 4° C. After removal of reagent, cells were washed three times with wash buffer (50 mM Tris, pH 7.5, 150 mM NaCl, 1 mM $MgCl_2$, 1 mM $CaCl_2$) and lysed in 1% Triton X-100 lysis buffer for one hour. Lysates were centrifuged for 15 minutes at 15,000×g. Nucleolin was precipitated as described above and eluted with Laemmli sample buffer (1% SDS, 100 mM $NH_4HCO_3$). Eluted proteins were separated by 8-20% SDS-PAGE and transferred to nitrocellulose. The nitrocellulose membranes were subsequently incubated, after blocking, with ExtrAvidin-peroxidase conjugates diluted 1:5,000 (Sigma) for one hour at room temperature. Signals were detected after incubation with ECL reagent and exposure to Biomax MR.

Nucleolin was also detected at the cell surface by FACS analysis with rabbit polyclonal anti-nucleolin antibody prepared against amino acids 221 to 232 of nucleolin (NCL3). Cells which were alive and intact as indicated by gating for cells that did not stain with propidium iodide demonstrated significant binding of the anti-nucleolin antibody (see FIG. 7B). As shown in the figure, the positive control anti-α5 integrin antibody gave a strong shift, reflecting a high level of cell surface expression of α5β1 integrin. Anti-nucleolin antibody also caused a significant shift of the FACS peak compared to the control, indicative of nucleolin cell-surface expression. These results demonstrate that nucleolin is expressed at the cell surface in MDA-MB-435 cells.

Rabbit polyclonal antibodies were raised against peptides synthesized according to the nucleolin sequence. NCL2, NCL3 and NCL4 were raised against amino acids 43-51, 221-232 and 393-407 of human nucleolin, respectively, and were affinity-purified on the immunizing peptide. Each polyclonal antibody immunoblotted the 110-kDa nucleolin band in cell extracts, and the anti-NCL2 and anti-NCL3 antibodies bound intact cells shown to express cell surface nucleolin.

FACS analysis of cell surface nucleolin was performed as follows. MDA-MB-435 cells ($1 \times 10^6$ cells/sample) were detached with EDTA and incubated with primary antibody (10 μg/ml) for 45 minutes on ice. Cells were washed with ice-cold phosphate-buffered saline (PBS) and incubated with Alexa-435 secondary antibody (1:50 in PBS). As a negative control, cells were incubated with secondary antibody only. After washing, cells were resuspended in 50 μl PBS containing 2 μg/ml propidium iodide to distinguish between living and dead cells. Analysis was performed with 10,000 cells per sample using a FACSCalibur flow cytometer (BD Biosciences; San Jose, Calif.).

Figure 8:
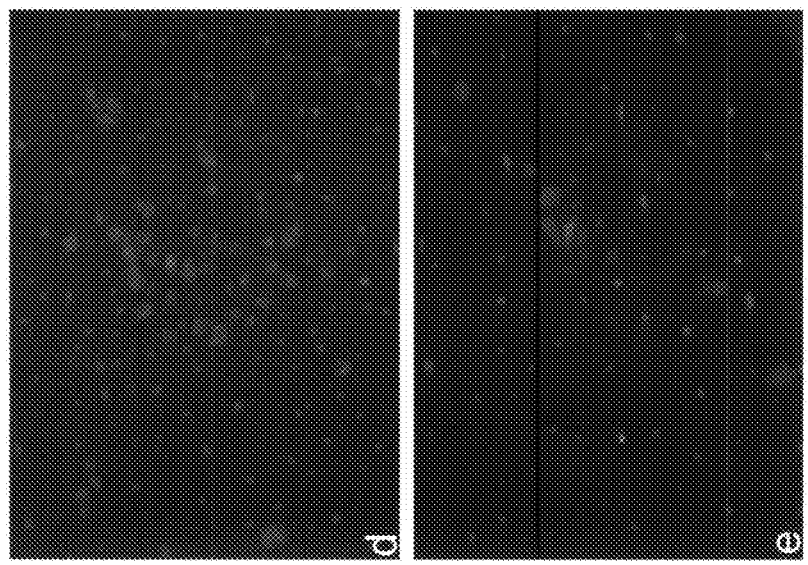
FIG. 8 shows that anti-nucleolin antibodies inhibit internalization of peptide SEQ ID NO: 9 into MDA-MB-435 cells. Exponentially growing cells were incubated with 1 µM FITC-SEQ ID NO: 9 (A,B,C) or FITC-LyP1 control peptide (D,E) for two hours at 37° C. and co-incubated with NCL3 anti-nucleolin antibody (B,D). FITC staining is shown in green; DAPI staining of nuclei is shown in blue.
Figure 8:
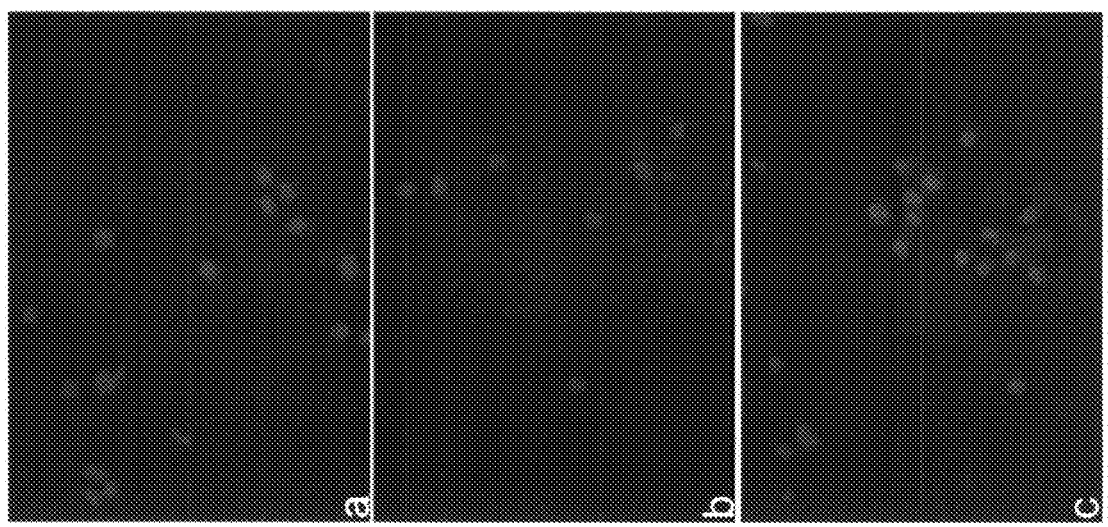

C. Inhibition of Peptide SEQ ID NO: 9 Internalization by Treatment of Cells with Anti-Nucleolin Antibodies Nucleolin has been observed to shuttle between the cytoplasm and the nucleus, or the cell surface and the nucleus (Shibata et al., *Mol. Cell. Biol.* 22:6788-6796 (2002), and Said et al., *J. Biol. Chem.* 277:37492-37502 (2002)). Fluorescein-labeled peptide was used to analyze nucleolin-dependence of SEQ ID NO: 9 localization. For internalization experiments, cells were incubated with FITC-labeled peptide (1 μM) for two hours at 37° C. After washing with PBS, cells were fixed with 4% paraformaldehyde (PFA) and analyzed by fluorescence microscopy. As shown in FIG. 8A, fluorescein-labeled peptide SEQ ID NO: 9 was taken up by MDA-MB-435 cells and localized to the nucleus. Thus, like other basic cell-penetrating peptides, the HMGN2 peptide SEQ ID NO: 9 is transported to the nucleus following internalization.

To analyze whether nucleolin is involved in internalization and nuclear transport of peptide SEQ ID NO: 9, cells were co-incubated with an anti-nucleolin antibody prepared against the amino-terminal acidic domain (NCL3) of nucleolin. As shown in FIG. 8B, co-incubation with anti-NCL3 antibodies abolished cellular uptake and nuclear localization of labeled peptide SEQ ID NO: 9. An anti-nucleolin antibody prepared by immunizing against NCL2 (amino acids 43-51), bound to intact nucleolin-expressing cells, but did not inhibit uptake or nuclear localization of peptide SEQ ID NO: 9 (see FIG. 8C). Moreover, the NCL3 antibody itself was internalized and transported into the nucleus, whereas the NCL2 antibody remained at the cell surface. Internalization of another peptide that binds MDA-MB-435 cells, FITC-LyP-1 (Laakkonen et al., *Nat. Med.* 8:751-755 (2002)), was not influenced by anti-nucleolin antibodies (FIGS. 8D and E). These results demonstrate that SEQ ID NO: 9 binds to the amino-terminal acidic domain of cell surface-expressed nucleolin and that internalization of HMGN2-derived peptides depends on nucleolin, which also may be responsible for nuclear transport. These results further demonstrate that anti-nucleolin antibodies also can be internalized by cells that express cell surface nucleolin.

D. Internalization of Peptide SEQ ID NO: 9 into MDA-MB-435 Cells is Independent of Heparin Sulfates Previous studies have show that binding to heparin sulfates can be sufficient for internalization of heparin sulfate-binding proteins (Roghani and Moscatelli, *J. Biol. Chem.* 267:22156-22162 (1992)). As described above, peptide SEQ ID NO: 9 is a highly basic molecule, suggesting that negatively charged cell surface glycosaminoglycans such as heparin sulfate may play a role in binding and internalization of this peptide.

Figure 9A:
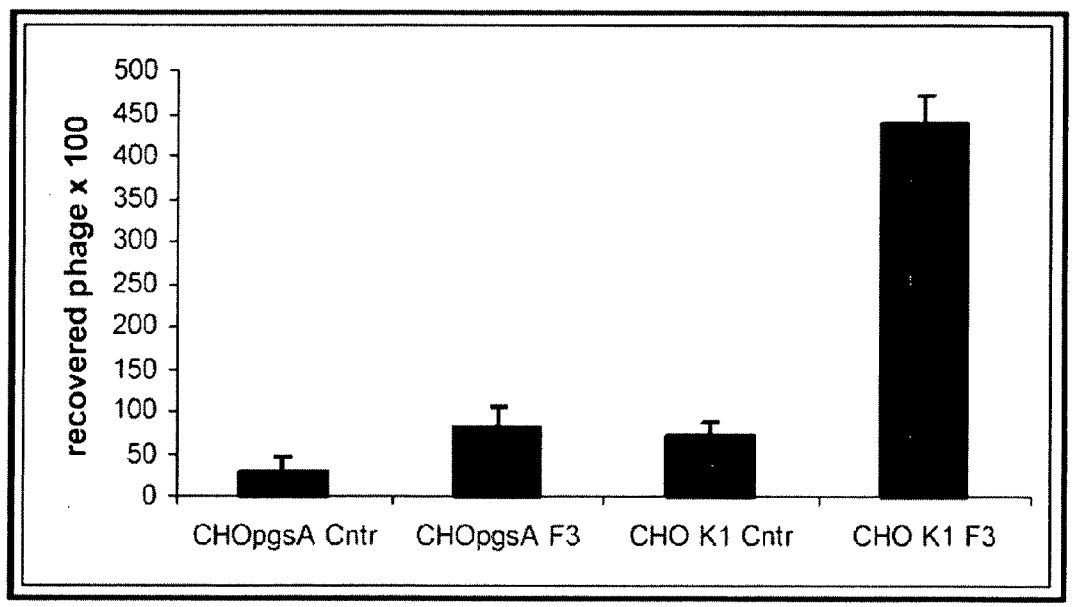
FIG. 9 shows that glycosaminoglycan-deficient cells bind and internalize peptide SEQ ID NO: 9. (A) Binding of SEQ ID NO: 9-displaying phage ("F3") to glycosaminoglycan-deficient pgsA-745 cells and parental CHO-K1 cells. (B) Immunofluorescence of FITC-labeled peptide SEQ ID NO: 9 or control peptide in CHO-K1 or pgsA-745 cells. Panel a: Control FITC-peptide in CHO-K1 cells. Panel b: FITC-labeled peptide SEQ ID NO: 9 in CHO-K1 cells. Panel c: Control FITC-labeled peptide in pgsA-745 cells. Panel d: FITC-labeled peptide SEQ ID NO: 9 in pgsA-745 cells.
Figure 9B:
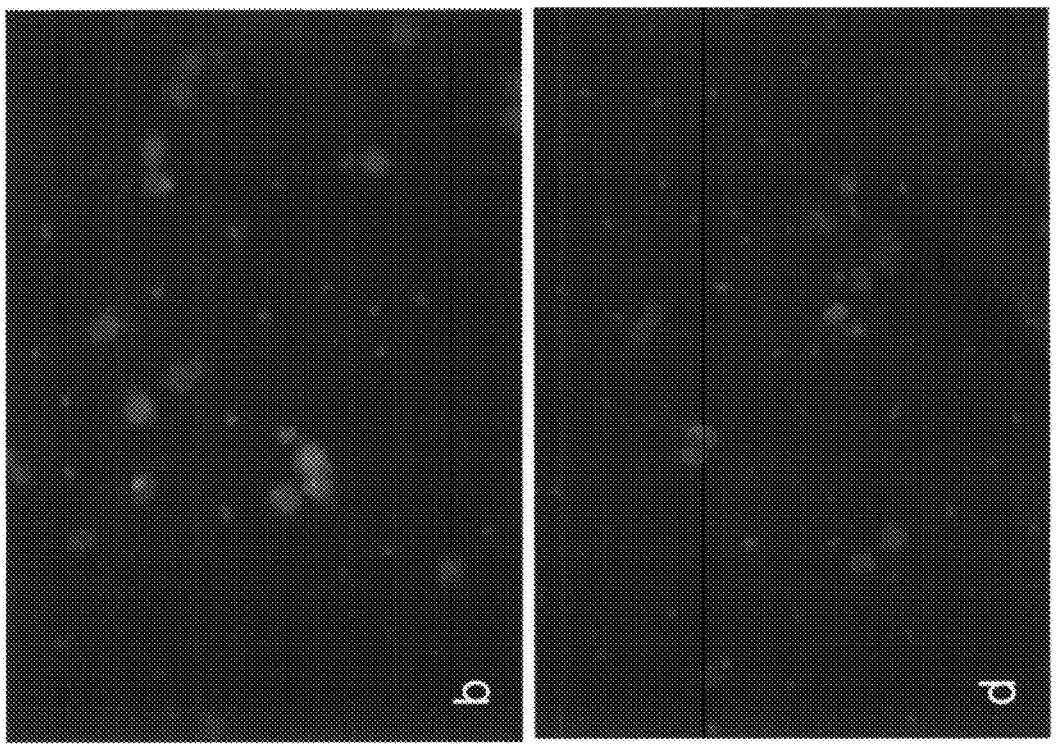
Figure 9B:
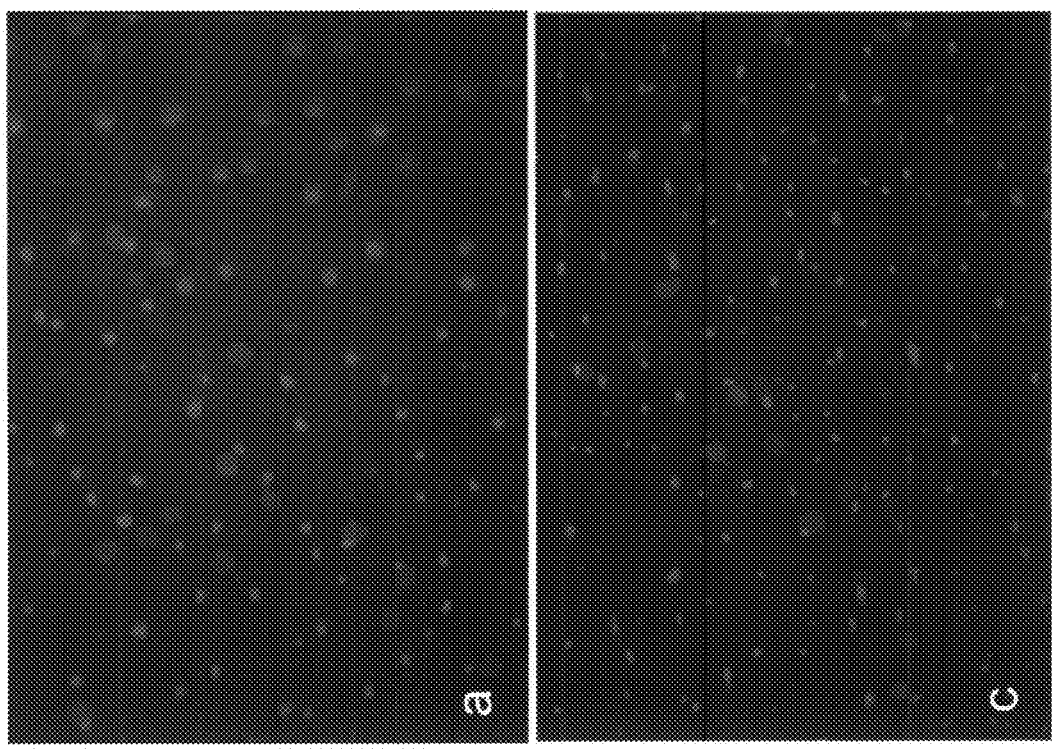

Cells that lack glycosaminoglycans including heparin sulfates due to a mutation in *xylosyl transferase* were assayed for the ability to bind and internalize peptide SEQ ID NO: 9. In particular, glycosaminoglycan-deficient pgsA-745 cells were assayed for the ability to bind SEQ ID NO: 9-displaying phage as an indication of SEQ ID NO: 9 peptide binding. As shown in FIG. 9A, SEQ ID NO:9-displaying phage bound to pgsA-745 cells at about 20% of the binding observed with corresponding wild type cells. SEQ ID NO: 9-phage binding to glycosaminoglycan-deficient cells was stronger than binding of non-recombinant control phage. Furthermore, glycosaminoglycan-deficient pgsA-745 cells incubated with FITC-labeled peptide SEQ ID NO: 9 showed equally efficient uptake and nuclear localization of peptide SEQ ID NO: 9 as did wild type cells. Neither cell type internalized fluorescein-labeled control peptide. In sum, these results indicate that glycosaminoglycans can contribute to cell surface binding of HMGN2-derived peptides. However, the demonstration that CHO cells lacking heparin sulfate and other glucosaminoglycans internalize SEQ ID NO: 9 efficiently excludes a direct role for heparin sulfate in cellular uptake of HMGN2-derived peptides such as SEQ ID NO: 9.

Binding of SEQ ID NO: 9-displaying phage to CHO-K1 and pgsA-745 cells was assayed as follows. CHO-K1 and pgsA-745 cells were grown in alpha MEM Earle's salt with 10% fetal calf serum and 1% Glutamine Pen-Strep (Irvine Scientific; Santa Ana, Calif.). After detaching cells with 2.5 mM EDTA, $10^6$ cells were incubated with $10^8$ phage for three hours on ice. Following extensive washing, bound phage were eluted by addition of 100 µl BLT5615 bacteria, and titers determined by routine methods.

E. Sub-Cellular Distribution of Nucleolin Changes Depending on Growth State

To test the hypothesis that localization of nucleolin is affected by the growth state of cells cultured in vitro, cells grown under different conditions were stained with anti-nucleolin antibodies. As shown in FIG. 10, anti-NCL3 (anti-nucleolin) antibody stained the surface of actively growing MDA-MB-435 cells; there was no surface staining of the MDA-MB-435 cells rendered stationary by serum withdrawal. Nuclear nucleolin was detected in permeabilized cells under both conditions. Thus, nucleolin is exclusively nuclear in serum-starved cells. These results demonstrate that nucleolin is selectively expressed on the cell surface of proliferating cells and indicate that nucleolin-binding molecules can be useful for selectively targeting moieties to actively dividing endothelial and tumor cells.

For nucleolin staining, cells were fixed with 4% paraformaldehyde and either directly stained with anti-NCL3 antibody (10 µg/ml) or stained following permeabilization with Triton X-100. Bound antibody was detected with Alexa-594 labeled anti-rabbit antibody (Molecular Probes; Eugene, Oreg.) and visualized by fluorescence microscopy.

F. Nucleolin is Expressed in Tumor Vasculature in Vivo

In vivo tissue expression of cell surface nucleolin was analyzed by injecting the anti-NCL3 antibody intravenously into mice. Tissues collected 60 minutes after the injection showed selective accumulation of the antibody in tumor blood vessels (FIGS. 11A and B), mimicking the distribution of peptide SEQ ID NO: 9 shown above. No anti-NCL3 antibody was detected in the blood vessels of various normal tissues (shown for the skin in FIG. 11C). A control antibody prepared in the same manner as the anti-nucleolin antibody did not appear in tumor blood vessels (see FIG. 11D). These results indicate that nucleolin is selectively expressed on the cell surface of tumor blood vessels in vivo.

In vivo distribution of cell surface nucleolin was examined using MDA-MB-435 xenografts generated by subcutaneous injection of $10^6$ exponentially growing cells in 200 µl culture media. Mice (Balb/c nu/nu; Animal Technologies, Ltd; Fremont, Calif.) were used for further experiments eight weeks after injection. Polyclonal rabbit anti-nucleolin antibody (200 µg) was injected into blood circulation of tumor bearing mice. After one hour of circulation, mice were sacrificed by perfusion of 10 ml PBS into the heart, followed by the injection of 4% PFA. Tumor and control tissues were removed and frozen in OCT embedding medium (Tissue-Tek; Elkhart, Ind.). Tissue sections of 5 µm were used for blood vessel staining with anti-CD31 antibody (Pharmingen; San Diego, Calif.). Injected rabbit antibody and anti-CD31 antibody were detected with Alexa-594 and Alexa-486 conjugated secondary antibodies, respectively, and examined under an inverted fluorescent microscope. Nuclei were counterstained using 4'6-diamidino-2-phenylindole (Vector; Burlingame, Calif.).

We claim:

1. An isolated homing peptide comprising the amino acid sequence KDEPQRRSARLSAKPAPPKPEPKPKKAPAKK (SEQ ID NO: 9) said peptide having a length of less than 70 residues, wherein said peptide specifically binds nucleolin expressed on the surface of a tumor cell.

2. The isolated peptide of claim 1, which has a length of less than 60 residues.

3. The isolated peptide of claim 1, which has a length of less than 50 residues.

4. The isolated peptide of claim 1, which has a length of less than 45 residues.

5. The isolated peptide of claim 1, which has a length of less than 40 residues.

6. The isolated peptide of claim 1, which has a length of less than 35 residues.

7. An isolated homing peptide that selectively homes to tumor blood vessels or tumor cells, comprising the amino acid sequence KDEPQRRSARLSAKPAPPKPEPKPKKAPAKK (SEQ ID NO: 9), said peptide having a length of less than 70 residues.

8. The isolated homing peptide of claim 7, which has a length of less than 60 residues.

9. The isolated homing peptide of claim 7, which has a length of less than 50 residues.

10. The isolated homing peptide of claim 7, which has a length of less than 45 residues.

11. The isolated homing peptide of claim 7, which has a length of less than 40 residues.

12. The isolated homing peptide of claim 7, which has a length of less than 35 residues.

13. An isolated peptide consisting of the amino acid sequence KDEPQRRSARLSAKPAPPKPEPKPKKAPAKK (SEQ ID NO: 9).

14. A chimeric polypeptide comprising a peptide consisting of the amino acid sequence KDEPQRRSARLSAKPAPPKPEPKPKKAPAKK (SEQ ID NO: 9) fused to a heterologous polypeptide, wherein said chimeric polypeptide specifically binds nucleolin.

15. A chimeric polypeptide comprising a peptide consisting of the amino acid sequence KDEPQRRSARLSAKPAPPKPEPKPKKAPAKK (SEQ ID NO: 9) fused to a heterologous polypeptide, wherein said chimeric polypeptide selectively homes to tumor blood vessels or tumor cells.

* * * * *

SEQUENCE LISTING

<160> NUMBER OF SEQ ID NOS: 20

<210> SEQ ID NO 1
<211> LENGTH: 81
<212> TYPE: PRT
<213> ORGANISM: Homo sapiens

<400> SEQUENCE: 1

Ala Lys Gly Asp Lys Ala Lys Val Lys Asp Glu Pro Gln Arg Arg Ser
 1               5                   10                  15

-continued

Ala Arg Leu Ser Ala Lys Pro Ala Pro Pro Lys Pro Glu Pro Lys Pro
            20                  25                  30

Lys Lys Ala Pro Ala Lys Lys Gly Glu Lys Ala Pro Lys Gly Lys Lys
        35                  40                  45

Gly Lys Ala Asp Ala Gly Lys Glu Gly Asn Asn Pro Ala Glu Asn Gly
    50                  55                  60

Asp Ala Lys Thr Asp Gln Ala Gln Lys Ala Glu Gly Ala Gly Asp Ala
65                  70                  75                  80

Lys

<210> SEQ ID NO 2
<211> LENGTH: 101
<212> TYPE: PRT
<213> ORGANISM: Homo sapeins

<400> SEQUENCE: 2

Ser Val Arg Arg Gly Glu Asn Asp Pro Arg Thr Asp Gln Ser Pro Arg
 1               5                  10                  15

Ala Ala Ala Ser Arg Val Gln His Leu Arg Pro Ala Ala Val Ala Ala
            20                  25                  30

Ala Thr Met Pro Lys Arg Lys Ala Glu Gly Asp Ala Lys Gly Asp Lys
        35                  40                  45

Ala Lys Val Lys Asp Glu Ser Pro Gln Arg Arg Ser Ala Arg Leu Ser
    50                  55                  60

Ala Lys Pro Ala Pro Pro Lys Pro Glu Pro Lys Pro Lys Lys Ala Pro
65                  70                  75                  80

Ala Lys Lys Gly Glu Lys Val Pro Lys Gly Lys Lys Gly Lys Ala Asp
                85                  90                  95

Ala Gly Lys Glu Gly
            100

<210> SEQ ID NO 3
<211> LENGTH: 75
<212> TYPE: PRT
<213> ORGANISM: Homo sapiens
<220> FEATURE:
<221> NAME/KEY: VARIANT
<222> LOCATION: 18, 36, 51, 58, 60, 67, 72, 73
<223> OTHER INFORMATION: Xaa = Any Amino Acid

<400> SEQUENCE: 3

Ser Pro Thr Gly Leu Leu Lys Pro Pro Ala Asn Thr Ala Ala Thr Met
 1               5                  10                  15

Pro Xaa Arg Lys Ala Lys Gly Asp Ala Lys Gly Asp Ile Ala Lys Val
            20                  25                  30

Lys Asp Glu Xaa His Arg Arg Ser Ala Arg Leu Ser Ala Lys Pro Ala
        35                  40                  45

Pro Pro Xaa Pro Glu Pro Arg Pro Lys Xaa Ala Xaa Ala Lys Lys Gly
    50                  55                  60

Asp Lys Xaa Ala Ala Ala Leu Xaa Xaa Leu Val
65                  70                  75

<210> SEQ ID NO 4
<211> LENGTH: 54
<212> TYPE: PRT
<213> ORGANISM: Homo sapiens
<220> FEATURE:
<221> NAME/KEY: VARIANT
<222> LOCATION: 19, 33, 39, 52

```
<223> OTHER INFORMATION: Xaa = Any Amino Acid

<400> SEQUENCE: 4

Ser Arg Lys Ser Ala Arg Leu Ser Ala Lys Pro Ala Pro Lys Pro
 1               5                  10                  15

Glu Pro Xaa Pro Lys Lys Gly Pro Ala Lys Lys Gly Glu Lys Val Pro
                20                  25                  30

Xaa Gly Lys Lys Gly Lys Xaa Asp Ala Gly Glu Asp Ala Glu Asn Gly
            35                  40                  45

Glu Gly Ser Xaa Tyr Thr
            50

<210> SEQ ID NO 5
<211> LENGTH: 88
<212> TYPE: PRT
<213> ORGANISM: Homo sapiens

<400> SEQUENCE: 5

Ala Ala Ser Arg Val Gln His Leu Arg Pro Ala Ala Val Ala Ala Ala
 1               5                  10                  15

Thr Met Pro Lys Arg Lys Ala Glu Gly Asp Ala Lys Gly Asp Lys Ala
                20                  25                  30

Lys Val Lys Asp Glu Pro Gln Arg Arg Ser Ala Arg Leu Ser Ala Lys
            35                  40                  45

Pro Ala Pro Pro Lys Pro Glu Pro Lys Pro Lys Lys Ala Pro Ala Lys
        50                  55                  60

Lys Gly Glu Lys Val Pro Lys Gly Lys Lys Gly Lys Ala Asp Ala Gly
65                  70                  75                  80

Lys Glu Gly Asn Asn Pro Ala Glu
                85

<210> SEQ ID NO 6
<211> LENGTH: 90
<212> TYPE: PRT
<213> ORGANISM: Homo sapiens

<400> SEQUENCE: 6

Met Pro Lys Arg Lys Ala Glu Gly Asp Ala Lys Gly Asp Lys Ala Lys
 1               5                  10                  15

Val Lys Asp Glu Pro Gln Arg Arg Ser Ala Arg Leu Ser Ala Lys Pro
                20                  25                  30

Ala Pro Pro Lys Pro Glu Pro Lys Pro Lys Lys Ala Pro Ala Lys Lys
            35                  40                  45

Gly Glu Lys Val Pro Lys Gly Lys Lys Gly Lys Ala Asp Ala Gly Lys
        50                  55                  60

Glu Gly Asn Asn Pro Ala Glu Asn Gly Asp Ala Lys Thr Asp Gln Ala
65                  70                  75                  80

Gln Lys Ala Glu Gly Ala Gly Asp Ala Lys
                85                  90

<210> SEQ ID NO 7
<211> LENGTH: 17
<212> TYPE: PRT
<213> ORGANISM: Homo sapiens

<400> SEQUENCE: 7

Ala Ala Ser Arg Val Gln His Leu Arg Pro Ala Ala Val Ala Ala Ala
 1               5                  10                  15
```

Thr

<210> SEQ ID NO 8
<211> LENGTH: 17
<212> TYPE: PRT
<213> ORGANISM: Homo sapiens

<400> SEQUENCE: 8

Met Pro Lys Arg Lys Ala Glu Gly Asp Ala Lys Gly Asp Lys Ala Lys
1               5                   10                  15

Val

<210> SEQ ID NO 9
<211> LENGTH: 31
<212> TYPE: PRT
<213> ORGANISM: Homo sapiens

<400> SEQUENCE: 9

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 10
<211> LENGTH: 23
<212> TYPE: PRT
<213> ORGANISM: Homo sapiens

<400> SEQUENCE: 10

Gly Glu Lys Val Pro Lys Gly Lys Lys Gly Lys Ala Asp Ala Gly Lys
1               5                   10                  15

Glu Gly Asn Asn Pro Ala Glu
            20

<210> SEQ ID NO 11
<211> LENGTH: 10
<212> TYPE: PRT
<213> ORGANISM: Homo sapiens

<400> SEQUENCE: 11

Pro Gln Arg Arg Ser Ala Arg Leu Ser Ala
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic construct

<400> SEQUENCE: 12

Pro Lys Arg Arg Ser Ala Arg Leu Ser Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic construct

<400> SEQUENCE: 13

Ala Arg Ala Leu Pro Ser Gln Arg Ser Arg
1               5                   10

-continued

<210> SEQ ID NO 14
<211> LENGTH: 14
<212> TYPE: PRT
<213> ORGANISM: Artificial Sequence
<220> FEATURE:
<223> OTHER INFORMATION: synthetic construct

<400> SEQUENCE: 14

Lys Leu Ala Lys Leu Ala Lys Lys Leu Ala Lys Leu Ala Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthetic construct

<400> SEQUENCE: 15

Lys Leu Ala Lys Lys Leu Ala Lys Leu Ala Lys Lys Leu Ala
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic construct

<400> SEQUENCE: 16

Lys Ala Ala Lys Lys Ala Ala Lys Ala Ala Lys Lys Ala Ala
1               5                   10

<210> SEQ ID NO 17
<211> LENGTH: 21
<212> TYPE: PRT
<213> ORGANISM: Artificial Sequence
<220> FEATURE:
<223> OTHER INFORMATION: synthetic construct

<400> SEQUENCE: 17

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 18
<211> LENGTH: 2518
<212> TYPE: DNA
<213> ORGANISM: Homo sapiens
<220> FEATURE:
<221> NAME/KEY: CDS
<222> LOCATION: (112)...(2235)

<400> SEQUENCE: 18
cttcgggtgt acgtgctccg ggatcttcag cacccgcggc cgccatcgcc gtcgcttggc        60
ttcttctgga ctcatctgcg ccacttgtcc gcttcacact ccgccgccat c atg gtg       117
                                                         Met Val
                                                           1 aag ctc gcg aag gca ggt aaa aat caa ggt gac ccc aag aaa atg gct        165
Lys Leu Ala Lys Ala Gly Lys Asn Gln Gly Asp Pro Lys Lys Met Ala
        5                   10                  15 cct cct cca aag gag gta gaa gaa gat agt gaa gat gag gaa atg tca        213
Pro Pro Pro Lys Glu Val Glu Glu Asp Ser Glu Asp Glu Glu Met Ser -continued

```
            20                  25                  30
gaa gat gaa gaa gat gat agc agt gga gaa gag gtc gtc ata cct cag      261
Glu Asp Glu Glu Asp Asp Ser Ser Gly Glu Glu Val Val Ile Pro Gln
 35                  40                  45                  50 aag aaa ggc aag aag gct gct gca acc tca gca aag aag gtg gtc gtt      309
Lys Lys Gly Lys Lys Ala Ala Ala Thr Ser Ala Lys Lys Val Val Val
                 55                  60                  65 tcc cca aca aaa aag gtt gca gtt gcc aca cca gcc aag aaa gca gct      357
Ser Pro Thr Lys Lys Val Ala Val Ala Thr Pro Ala Lys Lys Ala Ala
             70                  75                  80 gtc act cca ggc aaa aag gca gca gca aca cct gcc aag aag aca gtt      405
Val Thr Pro Gly Lys Lys Ala Ala Ala Thr Pro Ala Lys Lys Thr Val
         85                  90                  95 aca cca gcc aaa gca gtt acc aca cct ggc aag aag gga gcc aca cca      453
Thr Pro Ala Lys Ala Val Thr Thr Pro Gly Lys Lys Gly Ala Thr Pro
     100                 105                 110 ggc aaa gca ttg gta gca act cct ggt aag aag ggt gct gcc atc cca      501
Gly Lys Ala Leu Val Ala Thr Pro Gly Lys Lys Gly Ala Ala Ile Pro
 115                 120                 125                 130 gcc aag ggg gca aag aat ggc aag aat gcc aag aag gaa gac agt gat      549
Ala Lys Gly Ala Lys Asn Gly Lys Asn Ala Lys Lys Glu Asp Ser Asp
                 135                 140                 145 gaa gag gag gat gat gac agt gag gag gat gag gag gat gac gag gac      597
Glu Glu Glu Asp Asp Asp Ser Glu Glu Asp Glu Glu Asp Asp Glu Asp
             150                 155                 160 gag gat gag gat gaa gat gaa att gaa cca gca gcg atg aaa gca gca      645
Glu Asp Glu Asp Glu Asp Glu Ile Glu Pro Ala Ala Met Lys Ala Ala
         165                 170                 175 gct gct gcc cct gcc tca gag gat gag gac gat gag gat gac gaa gat      693
Ala Ala Ala Pro Ala Ser Glu Asp Glu Asp Asp Glu Asp Asp Glu Asp
     180                 185                 190 gat gag gat gac gat gac gat gag gaa gat gac tct gaa gaa gaa gct      741
Asp Glu Asp Asp Asp Asp Asp Glu Glu Asp Asp Ser Glu Glu Glu Ala
 195                 200                 205                 210 atg gag act aca cca gcc aaa gga aag aaa gct gca aaa gtt gtt cct      789
Met Glu Thr Thr Pro Ala Lys Gly Lys Lys Ala Ala Lys Val Val Pro
                 215                 220                 225 gtg aaa gcc aag aac gtg gct gag gat gaa gat gaa gaa gag gat gat      837
Val Lys Ala Lys Asn Val Ala Glu Asp Glu Asp Glu Glu Glu Asp Asp
             230                 235                 240 gag gac gag gat gac gac gac gac gaa gat gat gaa gat gat gat gat      885
Glu Asp Glu Asp Asp Asp Asp Asp Glu Asp Asp Glu Asp Asp Asp Asp
         245                 250                 255 gaa gat gat gag gag gag gaa gaa gag gag gag gaa gag cct gtc aaa      933
Glu Asp Asp Glu Glu Glu Glu Glu Glu Glu Glu Glu Pro Val Lys
     260                 265                 270 gaa gca cct gga aaa cga aag aag gaa atg gcc aaa cag aaa gca gct      981
Glu Ala Pro Gly Lys Arg Lys Lys Glu Met Ala Lys Gln Lys Ala Ala
 275                 280                 285                 290 cct gaa gcc aag aaa cag aaa gtg gaa ggc aca gaa ccg act acg gct     1029
Pro Glu Ala Lys Lys Gln Lys Val Glu Gly Thr Glu Pro Thr Thr Ala
                 295                 300                 305 ttc aat ctc ttt gtt gga aac cta aac ttt aac aaa tct gct cct gaa     1077
Phe Asn Leu Phe Val Gly Asn Leu Asn Phe Asn Lys Ser Ala Pro Glu
             310                 315                 320 tta aaa act ggt atc agc gat gtt ttt gct aaa aat gat ctt gct gtt     1125
Leu Lys Thr Gly Ile Ser Asp Val Phe Ala Lys Asn Asp Leu Ala Val
         325                 330                 335 gtg gat gtc aga att ggt atg act agg aaa ttt ggt tat gtg gat ttt     1173
```

```
         Val Asp Val Arg Ile Gly Met Thr Arg Lys Phe Gly Tyr Val Asp Phe
             340                 345                 350 gaa tct gct gaa gac ctg gag aaa gcg ttg gaa ctc act ggt ttg aaa            1221
Glu Ser Ala Glu Asp Leu Glu Lys Ala Leu Glu Leu Thr Gly Leu Lys
355                 360                 365                 370 gtc ttt ggc aat gaa att aaa cta gag aaa cca aaa gga aaa gac agt            1269
Val Phe Gly Asn Glu Ile Lys Leu Glu Lys Pro Lys Gly Lys Asp Ser
                375                 380                 385 aag aaa gag cga gat gcg aga aca ctt ttg gct aaa aat ctc cct tac            1317
Lys Lys Glu Arg Asp Ala Arg Thr Leu Leu Ala Lys Asn Leu Pro Tyr
                390                 395                 400 aaa gtc act cag gat gaa ttg aaa gaa gtg ttt gaa gat gct gcg gag            1365
Lys Val Thr Gln Asp Glu Leu Lys Glu Val Phe Glu Asp Ala Ala Glu
        405                 410                 415 atc aga tta gtc agc aag gat ggg aaa agt aaa ggg att gct tat att            1413
Ile Arg Leu Val Ser Lys Asp Gly Lys Ser Lys Gly Ile Ala Tyr Ile
420                 425                 430 gaa ttt aag aca gaa gct gat gca gag aaa acc ttt gaa gaa aag cag            1461
Glu Phe Lys Thr Glu Ala Asp Ala Glu Lys Thr Phe Glu Glu Lys Gln
435                 440                 445                 450 gga aca gag atc gat ggg cga tct att tcc ctg tac tat act gga gag            1509
Gly Thr Glu Ile Asp Gly Arg Ser Ile Ser Leu Tyr Tyr Thr Gly Glu
                455                 460                 465 aaa ggt caa aat caa gac tat aga ggt gga aag aat agc act tgg agt            1557
Lys Gly Gln Asn Gln Asp Tyr Arg Gly Gly Lys Asn Ser Thr Trp Ser
                470                 475                 480 ggt gaa tca aaa act ctg gtt tta agc aac ctc tcc tac agt gca aca            1605
Gly Glu Ser Lys Thr Leu Val Leu Ser Asn Leu Ser Tyr Ser Ala Thr
        485                 490                 495 gaa gaa act ctt cag gaa gta ttt gag aaa gca act ttt atc aaa gta            1653
Glu Glu Thr Leu Gln Glu Val Phe Glu Lys Ala Thr Phe Ile Lys Val
500                 505                 510 ccc cag aac caa aat ggc aaa tct aaa ggg tat gca ttt ata gag ttt            1701
Pro Gln Asn Gln Asn Gly Lys Ser Lys Gly Tyr Ala Phe Ile Glu Phe
515                 520                 525                 530 gct tca ttc gaa gac gct aaa gaa gct tta aat tcc tgt aat aaa agg            1749
Ala Ser Phe Glu Asp Ala Lys Glu Ala Leu Asn Ser Cys Asn Lys Arg
                535                 540                 545 gaa att gag ggc aga gca atc agg ctg gag ttg caa gga ccc agg gga            1797
Glu Ile Glu Gly Arg Ala Ile Arg Leu Glu Leu Gln Gly Pro Arg Gly
                550                 555                 560 tca cct aat gcc aga agc cag cca tcc aaa act ctg ttt gtc aaa ggc            1845
Ser Pro Asn Ala Arg Ser Gln Pro Ser Lys Thr Leu Phe Val Lys Gly
        565                 570                 575 ctg tct gag gat acc act gaa gag aca tta aag gag tca ttt gac ggc            1893
Leu Ser Glu Asp Thr Thr Glu Glu Thr Leu Lys Glu Ser Phe Asp Gly
580                 585                 590 tcc gtt cgg gca agg ata gtt act gac cgg gaa act ggg tcc tcc aaa            1941
Ser Val Arg Ala Arg Ile Val Thr Asp Arg Glu Thr Gly Ser Ser Lys
595                 600                 605                 610 ggg ttt ggt ttt gta gac ttc aac agt gag gag gat gcc aag gag gcc            1989
Gly Phe Gly Phe Val Asp Phe Asn Ser Glu Glu Asp Ala Lys Glu Ala
                615                 620                 625 atg gaa gac ggt gaa att gat gga aat aaa gtt acc ttg gac tgg gcc            2037
Met Glu Asp Gly Glu Ile Asp Gly Asn Lys Val Thr Leu Asp Trp Ala
                630                 635                 640 aaa cct aag ggt gaa ggt ggc ttc ggg ggt cgt ggt gga gga aga ggc            2085
Lys Pro Lys Gly Glu Gly Gly Phe Gly Gly Arg Gly Gly Gly Arg Gly
        645                 650                 655
```

-continued

```
ggc ttt gga gga cga ggt ggt ggt aga gga ggc cga gga ggt ttt ggt      2133
Gly Phe Gly Gly Arg Gly Gly Gly Arg Gly Gly Arg Gly Gly Phe Gly
    660                 665                 670 ggc aga ggc cgg gga ggc ttt gga ggg cga gga ggc ttc cga gga ggc      2181
Gly Arg Gly Arg Gly Gly Phe Gly Gly Arg Gly Gly Phe Arg Gly Gly
675                 680                 685                 690 aga gga gga gga ggt gac cac aag cca caa gga aag aag acg aag ttt      2229
Arg Gly Gly Gly Gly Asp His Lys Pro Gln Gly Lys Lys Thr Lys Phe
                695                 700                 705 gaa tag cttctgtccc tctgctttcc cttttccatt tgaaagaaag gactctgggg       2285
Glu * tttttactgt tacctgatca atgacagagc cttctgagga cattccaaga cagtatacag   2345
tcctgtggtc tccttggaaa tccgtctagt taacatttca agggcaatac cgtgttggtt   2405
ttgactggat attcatataa acttttttaaa gagttgagtg atagagctaa cccttatctg  2465
taagttttga atttatattg tttcatccca tgtacaaaac cattttttcc tac          2518

<210> SEQ ID NO 19
<211> LENGTH: 707
<212> TYPE: PRT
<213> ORGANISM: Homo sapiens

<400> SEQUENCE: 19

Met Val Lys Leu Ala Lys Ala Gly Lys Asn Gln Gly Asp Pro Lys Lys
1               5                   10                  15

Met Ala Pro Pro Lys Glu Val Glu Glu Asp Ser Glu Asp Glu Glu
            20                  25                  30

Met Ser Glu Asp Glu Glu Asp Ser Ser Gly Glu Glu Val Val Ile
        35                  40                  45

Pro Gln Lys Lys Gly Lys Lys Ala Ala Ala Thr Ser Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
    130                 135                 140

Ser Asp Glu Glu Glu Asp Asp Ser Glu Glu Asp Glu Glu Asp Asp
145                 150                 155                 160

Glu Asp Glu Asp Glu Asp Glu Asp Glu Ile Glu Pro Ala Ala Met Lys
                165                 170                 175

Ala Ala Ala Ala Ala Pro Ala Ser Glu Asp Glu Asp Asp Glu Asp Asp
            180                 185                 190

Glu Asp Asp Glu Asp Asp Asp Asp Glu Glu Asp Ser Glu Glu
        195                 200                 205

Glu Ala Met Glu Thr Thr Pro Ala Lys Gly Lys Lys Ala Ala Lys Val
    210                 215                 220

Val Pro Val Lys Ala Lys Asn Val Ala Glu Asp Glu Asp Glu Glu Glu
225                 230                 235                 240

Asp Asp Glu Asp Glu Asp Asp Asp Asp Glu Asp Glu Asp Glu Asp Asp
                245                 250                 255
```

-continued

```
Asp Asp Glu Asp Asp Glu Glu Glu Glu Glu Glu Glu Glu Pro
            260                 265                 270

Val Lys Glu Ala Pro Gly Lys Arg Lys Glu Met Ala Lys Gln Lys
        275                 280                 285

Ala Ala Pro Glu Ala Lys Lys Gln Lys Val Glu Gly Thr Glu Pro Thr
    290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
            340                 345                 350

Asp Phe Glu Ser Ala Glu Asp Leu Glu Lys Ala Leu Glu Leu Thr Gly
        355                 360                 365

Leu Lys Val Phe Gly Asn Glu Ile Lys Leu Glu Lys Pro Lys Gly Lys
    370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
            420                 425                 430

Tyr Ile Glu Phe Lys Thr Glu Ala Asp Ala Glu Lys Thr Phe Glu Glu
        435                 440                 445

Lys Gln Gly Thr Glu Ile Asp Gly Arg Ser Ile Ser Leu Tyr Tyr Thr
    450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
            500                 505                 510

Lys Val Pro Gln Asn Gln Asn Gly Lys Ser Lys Gly Tyr Ala Phe Ile
        515                 520                 525

Glu Phe Ala Ser Phe Glu Asp Ala Lys Glu Ala Leu Asn Ser Cys Asn
    530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
        595                 600                 605

Ser Lys Gly Phe Gly Phe Val Asp Phe Asn Ser Glu Glu Asp Ala Lys
    610                 615                 620

Glu Ala Met Glu Asp Gly Glu Ile Asp Gly Asn Lys Val Thr Leu Asp
625                 630                 635                 640

Trp Ala Lys Pro Lys Gly Glu Gly Gly Phe Gly Gly Arg Gly Gly Gly
                645                 650                 655

Arg Gly Gly Phe Gly Gly Arg Gly Gly Arg Gly Arg Gly Gly
            660                 665                 670

Phe Gly Gly Arg Gly Arg Gly Gly Phe Gly Gly Arg Gly Gly Phe Arg
```

```
                  675                 680                 685
Gly Gly Arg Gly Gly Gly Asp His Lys Pro Gln Gly Lys Lys Thr
        690                 695                 700

Lys Phe Glu
705

<210> SEQ ID NO 20
<211> LENGTH: 35
<212> TYPE: PRT
<213> ORGANISM: Artificial Sequence
<220> FEATURE:
<223> OTHER INFORMATION: synthetic construct

<400> SEQUENCE: 20

Ala Pro Lys Asp Lys Pro Ala Ala Val Lys Glu Arg Lys Lys Pro Ala
 1               5                  10                  15

Pro Lys Pro Arg Pro Gln Glu Leu Arg Ser Lys Lys Ala Lys Pro Ala
            20                  25                  30

Pro Ala Ser
        35
```